(12) United States Patent
Kim et al.

(10) Patent No.: US 10,548,828 B2
(45) Date of Patent: Feb. 4, 2020

(54) USE OF 3,6-ANHYDRO-L-GALACTOSE FOR PREVENTING DENTAL CARIES

(71) Applicant: Korea University Research and Business Foundation, Seoul (KR)

(72) Inventors: Kyoung Heon Kim, Seoul (KR); In-Geol Choi, Seoul (KR); Eun-Ju Yun, Seoul (KR); Ah-Reum Lee, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 0 days.

(21) Appl. No.: 15/764,732

(22) PCT Filed: Oct. 14, 2016

(86) PCT No.: PCT/KR2016/011530
§ 371 (c)(1),
(2) Date: Mar. 29, 2018

(87) PCT Pub. No.: WO2017/065546
PCT Pub. Date: Apr. 20, 2017

(65) Prior Publication Data
US 2018/0280272 A1    Oct. 4, 2018

(30) Foreign Application Priority Data
Oct. 16, 2015    (KR) .................. 10-2015-0144679

(51) Int. Cl.
| | |
|---|---|
| *A61K 8/60* | (2006.01) |
| *A61K 31/7004* | (2006.01) |
| *A61K 9/00* | (2006.01) |
| *A61Q 11/00* | (2006.01) |
| *A23L 33/125* | (2016.01) |

(52) U.S. Cl.
CPC .............. *A61K 8/60* (2013.01); *A23L 33/125* (2016.08); *A61K 9/0056* (2013.01); *A61K 31/7004* (2013.01); *A61Q 11/00* (2013.01); *A23V 2002/00* (2013.01)

(58) Field of Classification Search
CPC .... A61K 8/60; A61K 9/0056; A61K 31/7004; A23L 33/125; A61Q 11/00; A23V 2002/00
See application file for complete search history.

(56) References Cited

U.S. PATENT DOCUMENTS

| | | | |
|---|---|---|---|
| 8,524,199 B2 * | 9/2013 | Randive ................ | A61K 8/19 424/401 |
| 2009/0092565 A1 | 4/2009 | Koyama et al. | |
| 2014/0314905 A1 | 10/2014 | Mo et al. | |

FOREIGN PATENT DOCUMENTS

| | | |
|---|---|---|
| KR | 20100040438 A | 4/2010 |
| KR | 20100108241 A | 10/2010 |
| KR | 2012-0085364 A | 8/2012 |
| KR | 20130085017 A | 7/2013 |
| KR | 20150043040 A | 4/2015 |

OTHER PUBLICATIONS

Loesche et al., "Association of *Streptococcus mutans* with Human Dental Decay," Infection and Immunity (Jun. 1975); 11(6):1252-1260.

Trahan et. al., "Transport and Phosphorylation of Xylitol by a Fructose Phosphotransferase System in *Streptococcus mutans*," Caries Res. (1985); 19:53-63.

Knuuttila et. al., "Effect of Xylitol on the Growth and Metabolism of *Streptococcus mutants*," Caries Res. (1975); 9:177-189.

Fujiwara et al., "Development of a minimal medium for *Streptococcus mutans*," Archs Oral Biol. (1978) 23:601-602.

* cited by examiner

*Primary Examiner* — Lezah Roberts

(74) *Attorney, Agent, or Firm* — Fox Rothschild LLP

(57) ABSTRACT

The present invention relates to a use of 3,6-anhydro-L-galactose for preventing dental caries. More specifically, 3,6-anhydro-L-galactose inhibits the growth of oral microorganisms and exhibits anti-caries activity to inhibit the production of acids caused by the consumption of a carbon source by the oral microorganisms. Thus, 3,6-anhydro-L-galactose can be used in pharmaceuticals, food products, oral hygiene preparations, etc. for preventing, ameliorating or treating oral diseases caused by oral microorganisms, such as dental caries, gingivitis, periodontitis, oral mucosal ulcer, halitosis or xerostomia.

4 Claims, 19 Drawing Sheets

Specification includes a Sequence Listing.

SEQUENCE LISTING

<160> NUMBER OF SEQ ID NOS: 3

<210> SEQ ID NO 1
<211> LENGTH: 747
<212> TYPE: PRT
<213> ORGANISM: Saccharophagus degradans 2-40T

<400> SEQUENCE: 1

Met Leu Phe Asp Phe Glu Asn Asp Gln Val Pro Ser Asn Ile His Phe
1               5                   10                  15

Leu Asn Ala Arg Ala Ser Ile Glu Thr Tyr Thr Gly Ile Asn Gly Glu
            20                  25                  30

Pro Ser Lys Gly Leu Lys Leu Ala Met Gln Ser Lys Gln His Ser Tyr

-continued

```
                35                  40                  45
Thr Gly Leu Ala Ile Val Pro Glu Gln Pro Trp Asp Trp Ser Glu Phe
 50                  55                  60
Thr Ser Ala Ser Leu Tyr Phe Asp Ile Val Ser Val Gly Asp His Ser
 65                  70                  75                  80
Thr Gln Phe Tyr Leu Asp Val Thr Asp Gln Asn Gly Ala Val Phe Thr
                 85                  90                  95
Arg Ser Ile Asp Ile Pro Val Gly Lys Met Gln Ser Tyr Tyr Ala Lys
                100                 105                 110
Leu Ser Gly His Asp Leu Glu Val Pro Asp Ser Gly Asp Val Asn Asp
                115                 120                 125
Leu Asn Leu Ala Ser Gly Leu Arg Ser Asn Pro Pro Thr Trp Thr Ser
130                 135                 140
Asp Asp Arg Gln Phe Val Trp Met Trp Gly Val Lys Asn Leu Asp Leu
145                 150                 155                 160
Ser Gly Ile Ala Lys Ile Ser Leu Ser Val Gln Ser Ala Met His Asp
                165                 170                 175
Lys Thr Val Ile Ile Asp Asn Ile Arg Ile Gln Pro Asn Pro Pro Gln
                180                 185                 190
Asp Glu Asn Phe Leu Val Gly Leu Val Asp Glu Phe Gly Gln Asn Ala
                195                 200                 205
Lys Val Asp Tyr Lys Gly Lys Ile His Ser Leu Glu Glu Leu His Ala
210                 215                 220
Ala Arg Asp Val Glu Leu Ala Glu Leu Asp Gly Lys Pro Met Pro Ser
225                 230                 235                 240
Arg Ser Lys Phe Gly Gly Trp Leu Ala Gly Pro Lys Leu Lys Ala Thr
                245                 250                 255
Gly Tyr Phe Arg Thr Glu Lys Ile Asn Gly Lys Trp Met Leu Val Asp
                260                 265                 270
Pro Glu Gly Tyr Pro Tyr Phe Ala Thr Gly Leu Asp Ile Ile Arg Leu
                275                 280                 285
Ser Asn Ser Ser Thr Met Thr Gly Tyr Asp Tyr Asp Gln Ala Thr Val
290                 295                 300
Ala Gln Arg Ser Ala Asp Val Thr Pro Glu Asp Ser Lys Gly Leu
305                 310                 315                 320
Met Ala Val Ser Glu Lys Ser Phe Ala Thr Arg His Leu Ala Ser Pro
                325                 330                 335
Thr Arg Ala Ala Met Phe Asn Trp Leu Pro Asp Tyr Asp His Pro Leu
                340                 345                 350
Ala Asn His Tyr Asn Tyr Arg Arg Ser Ala His Ser Gly Pro Leu Lys
                355                 360                 365
Arg Gly Glu Ala Tyr Ser Phe Tyr Ser Ala Asn Leu Glu Arg Lys Tyr
                370                 375                 380
Gly Glu Thr Tyr Pro Gly Ser Tyr Leu Asp Lys Trp Arg Glu Val Thr
385                 390                 395                 400
Val Asp Arg Met Leu Asn Trp Gly Phe Thr Ser Leu Gly Asn Trp Thr
                405                 410                 415
Asp Pro Ala Tyr Tyr Asp Asn Asn Arg Ile Pro Phe Phe Ala Asn Gly
                420                 425                 430
Trp Val Ile Gly Asp Phe Lys Thr Val Ser Ser Gly Ala Asp Phe Trp
                435                 440                 445
Gly Ala Met Pro Asp Val Phe Asp Pro Glu Phe Lys Val Arg Ala Met
450                 455                 460
```

-continued

Glu Thr Ala Arg Val Val Ser Glu Glu Ile Lys Asn Ser Pro Trp Cys
465                 470                 475                 480

Val Gly Val Phe Ile Asp Asn Glu Lys Ser Phe Gly Arg Pro Asp Ser
                485                 490                 495

Asp Lys Ala Gln Tyr Gly Ile Pro Ile His Thr Leu Gly Arg Pro Ser
            500                 505                 510

Glu Gly Val Pro Thr Arg Gln Ala Phe Ser Lys Leu Leu Lys Ala Lys
            515                 520                 525

Tyr Lys Thr Ile Ala Ala Leu Asn Asn Ala Trp Gly Leu Lys Leu Ser
            530                 535                 540

Ser Trp Ala Glu Phe Asp Leu Gly Val Asp Val Lys Ala Leu Pro Val
545                 550                 555                 560

Thr Asp Thr Leu Arg Ala Asp Tyr Ser Met Leu Leu Ser Ala Tyr Ala
                565                 570                 575

Asp Gln Tyr Phe Lys Val Val His Gly Ala Val Glu His Tyr Met Pro
            580                 585                 590

Asn His Leu Tyr Leu Gly Ala Arg Phe Pro Asp Trp Gly Met Pro Met
            595                 600                 605

Glu Val Val Lys Ala Ala Ala Lys Tyr Ala Asp Val Val Ser Tyr Asn
            610                 615                 620

Ser Tyr Lys Glu Gly Leu Pro Lys Gln Lys Trp Ala Phe Leu Ala Glu
625                 630                 635                 640

Leu Asp Lys Pro Ser Ile Ile Gly Glu Phe His Ile Gly Ala Met Asp
                645                 650                 655

His Gly Ser Tyr His Pro Gly Leu Ile His Ala Ala Ser Gln Ala Asp
            660                 665                 670

Arg Gly Glu Met Tyr Lys Asp Tyr Met Gln Ser Val Ile Asp Asn Pro
            675                 680                 685

Tyr Phe Val Gly Ala His Trp Phe Gln Tyr Met Asp Ser Pro Leu Thr
            690                 695                 700

Gly Arg Ala Tyr Asp Gly Glu Asn Tyr Asn Val Gly Phe Val Asp Val
705                 710                 715                 720

Thr Asp Thr Pro Tyr Gln Glu Met Val Asp Ala Ala Lys Glu Val Asn
                725                 730                 735

Ala Lys Ile Tyr Thr Glu Arg Leu Gly Ser Lys
            740                 745

<210> SEQ ID NO 2
<211> LENGTH: 806
<212> TYPE: PRT
<213> ORGANISM: Vibrio sp. EJY3

<400> SEQUENCE: 2

Met His Asn Ser Pro Arg Ser Thr Thr Leu Phe Asn Asp Asn Trp Leu
1               5                   10                  15

Phe Gln Leu Ala Lys Asp Lys Pro Asn Thr Lys Gln Trp Ser Thr Val
                20                  25                  30

Thr Leu Pro His Asp Trp Ser Val Ala Ser Phe Ser Pro Gln Tyr
            35                  40                  45

Asp Gly Ala Thr Gly Tyr Leu Pro Gly Gly Ile Gly Trp Tyr Lys Lys
            50                  55                  60

Gln Phe Lys Asn Pro Leu Asn Lys His Tyr Ser Arg Cys Ile Leu Val
65                  70                  75                  80

Phe Asp Gly Ile Tyr Asn Asn Ala Thr Ile Asn Ile Asn Gly Tyr Asp

```
                         85                  90                  95
Ile His Phe Gln Ala Tyr Gly Tyr Ala Pro Phe Asn Ile Glu Ile Thr
                    100                 105                 110

Asp Tyr Leu Lys Ser Asp Asn Val Ile Thr Ile His Val Asp Arg Arg
                    115                 120                 125

Arg Tyr Ile Asp Ser Arg Trp Tyr Thr Gly Ser Gly Ile Tyr Arg Asp
                    130                 135                 140

Ile Glu Met Val Leu Thr Lys Asp Val Phe Val Pro Ile Trp Glu Asn
145                 150                 155                 160

His Ile Lys Ala Ser Val Ser Ser Asn Gln Ile Gly His Ile His Gln
                    165                 170                 175

Gln Leu Met Ile Glu Ala Lys Thr Lys Thr His Tyr Leu Thr Ile Val
                    180                 185                 190

Ser Arg Leu Leu Glu Pro Asn Ser Asp Asn Cys Val Ala Thr Ala Arg
                    195                 200                 205

Thr His Arg Ser Val Asn Asn Arg Glu Val Cys Asp Leu Glu Leu Thr
                    210                 215                 220

Cys Asp Gln Leu Ser Leu Trp Ser Pro Asp Ser Pro Ile Leu Tyr Lys
225                 230                 235                 240

Leu Glu Thr Gln Ile Tyr Glu Asn Gly Cys Val Ile Asp Lys Val Ser
                    245                 250                 255

Glu Asn Ile Gly Phe Arg Ser Ile Glu Phe Ser Pro Gln Gly Phe
                    260                 265                 270

Phe Leu Asn Gly Met Pro Thr Lys Val Arg Gly Val Cys Leu His His
                    275                 280                 285

Asp Gly Gly Leu Val Gly Ala Ala Val Pro Asp Glu Ile Trp Ile Arg
                    290                 295                 300

Arg Leu Ser Lys Leu Lys Gln Cys Gly Val Asn Ala Ile Arg Ile Ala
305                 310                 315                 320

His Asn Pro Ala Ser Lys Arg Leu Leu His Leu Cys Asp Thr Met Gly
                    325                 330                 335

Phe Leu Val Gln Asp Glu Phe Phe Asp Glu Trp Asp Tyr Pro Lys Asp
                    340                 345                 350

Lys Arg Leu Asn Met Gly Asn Gln His Asp Asp Phe Phe Ser Gln Cys
                    355                 360                 365

Tyr Thr Glu His Phe Gln Thr Arg Ala Lys Thr Asp Leu Cys Asn Thr
                    370                 375                 380

Leu Lys Cys His Ile Asn His Pro Ser Ile Phe Met Trp Ser Ile Gly
385                 390                 395                 400

Asn Glu Ile Glu Trp Thr Tyr Pro Arg Asn Val Glu Ala Thr Gly Phe
                    405                 410                 415

Phe Asp Ala Ser Trp Asp Gly Asn Tyr Phe Trp Ser Leu Pro Pro Asn
                    420                 425                 430

Ser Pro Asp Glu Ile Lys Asp Lys Leu Lys Asn Leu Pro Gln His Thr
                    435                 440                 445

Tyr Asp Ile Gly Lys Thr Ala Asn Lys Leu Ala Arg Trp Val Lys Ala
                    450                 455                 460

Ile Asp Gln Thr Arg Pro Ile Thr Ala Asn Cys Ile Leu Pro Ser Ser
465                 470                 475                 480

Ser Tyr His Ser Gly Tyr Ala Asp Ala Leu Asp Val Ile Gly Phe Ser
                    485                 490                 495

Tyr Arg Arg Val Val Tyr Asp Tyr Gly His Glu Ile Arg Pro Asn Leu
                    500                 505                 510
```

```
Pro Ile Ile Gly Asn Glu Asn Leu Pro Gln Trp His Glu Trp Lys Ala
            515                 520                 525

Val Leu Glu Arg Asn His Val Ser Gly Leu Phe Leu Trp Thr Gly Ile
        530                 535                 540

Asn Tyr Met Gly Glu Ser His Gly Lys Trp Pro Val Arg Thr Thr Asp
545                 550                 555                 560

Ser Gly Leu Leu Asp Thr Ala Gly Phe Glu Lys Pro Ser Tyr Ala Leu
                565                 570                 575

Phe Lys Ser Leu Trp Thr Asp Glu Pro Tyr Val Lys Val Phe Thr Gln
                580                 585                 590

Arg Ala Asp Leu Thr Gln Leu Lys Phe Asp Glu Gln Thr Phe Val Ala
                595                 600                 605

Phe Glu His Asp Glu Asn Ala Trp Gln Lys Lys Leu Trp Val Trp Asp
            610                 615                 620

Glu Arg Asn Ser His Trp Asn Tyr Glu Asn Glu Gln Trp Val Thr Ile
625                 630                 635                 640

Glu Ala Tyr Ser Asn Cys Pro Gln Val Gln Leu Tyr Leu Asn Asp Glu
                645                 650                 655

Leu Val Gly Thr Gln Gln Leu Glu Lys Gln Ile Asp Arg Val Phe Arg
                660                 665                 670

Trp Ala Leu Pro Tyr Arg Ala Gly Lys Ile Ser Leu Val Gly Leu Lys
            675                 680                 685

Asn Asp Val Glu Val Thr Arg Asp Glu Ile Val Thr Ser Gly Val Pro
690                 695                 700

Arg Lys Ile Ser Ile Val Asp Glu Thr His Glu Gly Ser Ser Ser Tyr
705                 710                 715                 720

Arg Gln Leu Ile Val Gln Met Leu Asp Lys Asp Asn His Pro Val Ser
                725                 730                 735

His Glu Glu Ala Leu Leu Glu Phe Arg Val Arg Gly Cys Glu Trp Ile
            740                 745                 750

Gly Ala Asp Asn Gly Ser Ile Ser Ser Ile Asn Ala Tyr Asn Ser Pro
            755                 760                 765

Thr Ile Ala Thr Arg His Gly Arg Val Leu Ala Val Val Lys Ser Ser
        770                 775                 780

Gln Gly Gln Ser Gly Asp Ile Glu Ile Tyr Ser Asn Ser Gly Val Lys
785                 790                 795                 800

Ala Ser Phe Ser Leu Leu
                805

<210> SEQ ID NO 3
<211> LENGTH: 368
<212> TYPE: PRT
<213> ORGANISM: Saccharophagus degradans 2-40T

<400> SEQUENCE: 3

Met Ser Asp Ser Lys Val Asn Lys Lys Leu Ser Lys Ala Ser Leu Arg
1               5                   10                  15

Ala Ile Glu Arg Gly Tyr Asp Glu Lys Gly Pro Glu Trp Leu Phe Glu
                20                  25                  30

Phe Asp Ile Thr Pro Leu Lys Gly Asp Leu Ala Tyr Glu Glu Gly Val
            35                  40                  45

Ile Arg Arg Asp Pro Ser Ala Val Leu Lys Val Asp Asp Glu Tyr His
        50                  55                  60

Val Trp Tyr Thr Lys Gly Glu Gly Glu Thr Val Gly Phe Gly Ser Asp
```

-continued

```
            65                  70                  75                  80
Asn Pro Glu Asp Lys Val Phe Pro Trp Asp Lys Thr Glu Val Trp His
                85                  90                  95
Ala Thr Ser Lys Asp Lys Ile Thr Trp Lys Glu Ile Gly Pro Ala Ile
               100                 105                 110
Gln Arg Gly Ala Ala Gly Ala Tyr Asp Asp Arg Ala Val Phe Thr Pro
               115                 120                 125
Glu Val Leu Arg His Asn Gly Thr Tyr Tyr Leu Val Tyr Gln Thr Val
               130                 135                 140
Lys Ala Pro Tyr Leu Asn Arg Ser Leu Glu His Ile Ala Ile Ala Tyr
145                150                 155                 160
Ser Asp Ser Pro Phe Gly Pro Trp Thr Lys Ser Asp Ala Pro Ile Leu
               165                 170                 175
Ser Pro Glu Asn Asp Gly Val Trp Asp Thr Asp Glu Asp Asn Arg Phe
               180                 185                 190
Leu Val Lys Glu Lys Gly Ser Phe Asp Ser His Lys Val His Asp Pro
               195                 200                 205
Cys Leu Met Phe Phe Asn Asn Arg Phe Tyr Leu Tyr Tyr Lys Gly Glu
               210                 215                 220
Thr Met Gly Glu Ser Met Asn Met Gly Gly Arg Glu Ile Lys His Gly
225                230                 235                 240
Val Ala Ile Ala Asp Ser Pro Leu Gly Pro Tyr Thr Lys Ser Glu Tyr
               245                 250                 255
Asn Pro Ile Thr Asn Ser Gly His Glu Val Ala Val Trp Pro Tyr Lys
               260                 265                 270
Gly Gly Met Ala Thr Met Leu Thr Thr Asp Gly Pro Glu Lys Asn Thr
               275                 280                 285
Cys Gln Trp Ala Glu Asp Gly Ile Asn Phe Asp Ile Met Ser His Ile
               290                 295                 300
Lys Gly Ala Pro Glu Ala Val Gly Phe Phe Arg Pro Glu Ser Asp Ser
305                310                 315                 320
Asp Asp Pro Ile Ser Gly Ile Glu Trp Gly Leu Ser His Lys Tyr Asp
               325                 330                 335
Ala Ser Trp Asn Trp Asn Tyr Leu Cys Phe Phe Lys Thr Arg Arg Gln
               340                 345                 350
Val Leu Asp Ala Gly Ser Tyr Gln Gln Thr Gly Asp Ser Gly Ala Val
               355                 360                 365
```

USE OF 3,6-ANHYDRO-L-GALACTOSE FOR PREVENTING DENTAL CARIES

BACKGROUND

1. Field of the Invention

The present invention relates to an anti-cariogenic use of 3,6-anhydro-L-galactose that prevents or treats oral diseases by inhibiting the growth of oral microorganisms and suppressing acid production.

2. Discussion of Related Art

Dental caries is an oral disease which is one of the main causes of people visiting dentists and the incidence rate has been increased as mankind uses sugar as a sweetener. *Streptococcus mutans* is a main causative bacterium of dental caries (Loesche W J et al. (1975) *Infect Immun.* 11(6): 1252-60). *S. mutans* breaks sugar down in the oral cavity, and secretes a glucosyltransferase (GTF) to form insoluble glucans on the tooth surface, which leads to attachment of *S. mutans* or various other bacteria to the tooth surface to proliferate thereon. Bacteria on the tooth surface cause tooth decay as the enamel of the tooth surface is decalcified by an organic acid such as lactic acid, which is a carbohydrate metabolite (Dashper S G et al. (1996) *Microbiol.* 142, 33-29). As representative materials for preventing dental caries, fluoride compounds and xylitol, which prevent dental caries by reducing the number of *S. mutans* bacteria in dental plaque, are known (Trahan L et al. (1985) *Caries Res.* 19: 53-63). Xylitol, which is a 5-carbon alcohol present in nature, is produced as a gum and widely used due to sweetness similar to sugar and a sense of refreshment thereof, but it is disadvantageous in that the growth of *S. mutans* bacteria can be suppressed only in the case of a high concentration of xylitol.

Currently, research into natural materials having antimicrobial activity against *S. mutans* is increasingly conducted, and there is a growing interest in natural sugars as anti-cariogenic sweeteners, but research results on natural sugars which have an anti-cariogenic effect as much as xylitol are insufficient. When *S. mutans* ingests xylitol, xylitol-5-phophshate is formed by the activity of a phosphoenolpyruvate-xylitol phosphotrasferase system (PEP-xylitol PTS). The product inhibits the activity of a glycolytic enzyme and is no longer metabolized and thus is then extracellularly excreted in the form of xylitol, thus inhibiting bacterial growth and acid production via a futile cycle that does not generate energy and only consumes energy. At this time, the growth of *S. mutans* can be inhibited only with xylitol having a concentration of 25 g/L or more, and studies have also shown that resistant strains, the growth of which is not inhibited by xylitol, are produced when *S. mutans* is continuously cultured in a xylitol-containing medium (Knuuttila et al. (1975) Caries Research, 9(3), 177-189).

Therefore, there is a need to develop an anticariogenic agent capable of effectively inhibiting the growth of oral bacteria even at a low concentration without the formation of resistant strains.

SUMMARY OF THE INVENTION

An object of the present invention is to provide a pharmaceutical composition for preventing or treating an oral disease which includes 3,6-anhydro-L-galactose having activities of inhibiting the growth of oral organisms and acid production as an active ingredient, or a pharmaceutical composition for use in prevention or treatment of an oral disease.

Another object of the present invention is to provide a method of treating an oral disease by administering 3,6-anhydro-L-galactose to a subject in need thereof.

Still another object of the present invention is to provide an oral hygienic composition for preventing or alleviating an oral disease which includes 3,6-anhydro-L-galactose as an active ingredient.

Yet another object of the present invention is to provide a food composition for preventing or alleviating an oral disease which includes 3,6-anhydro-L-galactose as an active ingredient.

To achieve the above technical objects, the present invention provides a pharmaceutical composition for preventing or treating an oral disease, which includes 3,6-anhydro-L-galactose.

The present invention also provides a pharmaceutical composition for use in prevention or treatment of an oral disease, which includes 3,6-anhydro-L-galactose.

The present invention also provides a use of 3,6-anhydro-L-galactose for preparing the pharmaceutical composition for preventing or treating an oral disease.

The present invention also provides a method of treating an oral disease, including administering a pharmaceutically effective amount of the pharmaceutical composition for preventing or treating an oral disease to a subject in need thereof.

The present invention also provides an oral hygienic composition for preventing or alleviating an oral disease, which includes 3,6-anhydro-L-galactose.

The present invention also provides a food composition for preventing or alleviating an oral disease, which includes 3,6-anhydro-L-galactose.

3,6-Anhydro-L-galactose may be represented by Formula 1 below:

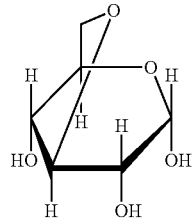

⟨Formula 1⟩

3,6-Anhydro-L-galactose may be obtained by reacting pretreated agarose with an enzyme mixture of an agarase, an agarolytic β-galactosidase, and an α-neoagarobiose hydrolase, or by separating and purifying a reaction product obtained by sequentially reacting pretreated agarose with an agarase, an agarolytic β-galactosidase, and an α-neoagarobiose hydrolase.

The pretreatment may be performed by reacting agarose with a weak acid at a temperature of 40° C. to 150° C. for 5 minutes to 6 hours.

The enzymatic reaction may be performed at a temperature of 20° C. to 40° C. for 30 minutes to 7 days.

The 3,6-anhydro-L-galactose may prevent, alleviate, or treat an oral disease by inhibiting the growth of one or more oral microorganism selected from the group consisting of *Streptococcus mutans, Streptococcus oralis, Streptococcus sanguinis, Fusobacterium nulcleatum, Porphyromonas gin-*

*givalis, Actinomyces viscosus, Actinobacillus actinomycetemcomitans*, and *Candida albicans* and acid production.

The oral microorganism may use one or more selected from the group consisting of glucose, sucrose, fructose, and maltose as a carbon source.

The oral disease may be any one selected from dental caries, gingivitis, periodontitis, oral mucous ulcers, halitosis, and xerostomia.

3,6-Anhydro-L-galactose of the present invention inhibits the growth of an oral microorganism and the generation of acid by carbon source consumption by an oral microorganism, and thus has an anticariogenic activity.

Accordingly, 3,6-anhydro-L-galactose can be used in medicines, foods, oral hygienic agents, and the like for preventing, alleviating, or treating an oral disease such as dental caries, gingivitis, periodontitis, oral mucous ulcers, halitosis, and xerostomia that occurs due to an oral microorganism.

BRIEF DESCRIPTION OF THE DRAWINGS

FIGS. 6*a* to 6*c*) or xylitol (0-40 g/L; FIGS. 6*d* to 6*f*).

DETAILED DESCRIPTION OF EXEMPLARY EMBODIMENTS

Figure 1:
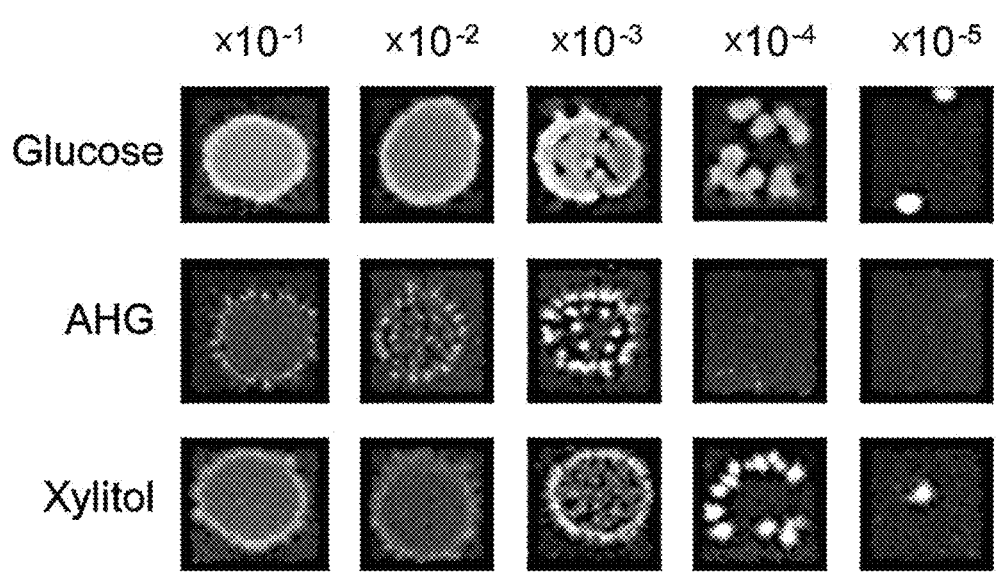
FIG. 1 illustrates an effect of a single carbon source on the growth of *Streptococcus mutans* in a liquid minimal medium or a solid minimal medium supplemented with each of 10 g/L of glucose, 10 g/L of 3,6-anhydro-L-galactose, and 10 g/L of xylitol as carbon sources (substrate conditions: 10 g/L of glucose; 10 g/L of 3,6-anhydro-L-galactose; and 10 g/L of xylitol, dilution factor: 10×, 100×, 1,000×, 10,000×, and 100,000×).

The inventors of the present invention pretreated agarose, produced galactose and 3,6-anhydro-L-galactose, which are monosaccharides, through enzymatic hydrolysis using three types of enzymes, and then separated and purified only 3,6-anhydro-L-galactose to be used as a carbon source for *Streptococcus mutans*. The inventors analyzed an anticariogenic effect of 3,6-anhydro-L-galactose by observing whether 3,6-anhydro-L-galactose inhibited the growth of *Streptococcus mutans* and acid production, and conducted comparative experiments using, as controls, xylitol and fermentable sugars such as sucrose, fructose, maltose, and the like, in addition to glucose, as carbon sources.

As a result, colony formation is inhibited under a 3,6-anhydro-L-galactose or xylitol condition as compared to a glucose condition, and in the case of highly diluted carbon sources, colonies were not formed under a 3,6-anhydro-L-galactose condition. In addition, 3,6-anhydro-L-galactose did not affect the growth promotion of *Streptococcus mutans*. Thus, it was confirmed that 3,6-anhydro-L-galactose is a non-fermentable sugar for *Streptococcus mutans* like xylitol, and had a much stronger growth inhibitory effect than xylitol. In addition, under conditions of carbon source mixtures of 3,6-anhydro-L-galactose and glucose, sucrose, fructose, maltose, or the like, 3,6-anhydro-L-galactose inhibited the growth of *Streptococcus mutans* at a low concentration thereof, while the growth of *Streptococcus mutans* did not occur at a high concentration of 3,6-anhydro-L-galactose. In addition, it was confirmed that at a low concentration (5 g/L) of 3,6-anhydro-L-galactose, the lag phase of *Streptococcus mutans* was increased, the growth rate thereof was reduced, and the concentration of produced acid was decreased, and thus 3,6-anhydro-L-galactose had a weak effect of inhibiting the cell growth of *Streptococcus mutans* and acid production, while, at a high concentration (10 g/L) of 3,6-anhydro-L-galactose, the growth of *Streptococcus mutans* and acid production were not observed at all, and there was no change in the concentration of 3,6-anhydro-L-galactose, and thus *Streptococcus mutans* was unable to use 3,6-anhydro-L-galactose as a carbon source. Meanwhile, as the concentration of xylitol known as a sugar to prevent dental caries increases, the growth of *Streptococcus mutans* is inhibited more. However, even under a much higher concentration, i.e., 40 g/L, than that of 3,6-anhydro-L-galactose, a considerable growth of *Streptococcus mutans* was observed, and acid production was not completely inhibited. This indicates that 3,6-anhydro-L-galactose has a much stronger effect of inhibiting the growth of *Streptococcus mutans* and acid production even at a lower concentration than xylitol.

Therefore, the present invention provides a pharmaceutical composition for preventing or treating an oral disease, which includes 3,6-anhydro-L-galactose.

The present invention also provides a pharmaceutical composition for use in preventing or treating an oral disease, which includes 3,6-anhydro-L-galactose.

The present invention also provides a use of 3,6-anhydro-L-galactose for preparing the pharmaceutical composition for preventing or treating an oral disease.

The 3,6-anhydro-L-galactose is a monosaccharide constituting agar, which is a representative carbohydrate component constituting red algae biomass, and may be obtained: through chemical synthesis; or by separating and purifying a reaction product obtained by reacting pretreated agarose with an enzyme mixture of an agarase, an agarolytic β-galactosidase, and an α-neoagarobiose hydrolase, or by sequentially reacting pretreated agarose with an agarase, an agarolytic β-galactosidase, and an α-neoagarobiose hydrolase.

The pretreatment of agarose may be performed by reacting agarose with a weak acid at a temperature of 40° C. to 150° C. for 5 min to 6 h. When the pretreatment conditions are within the above ranges, an excessive decomposition product of agarose by a weak acid and residual acetic acid may be minimized.

As the weak acid, acetic acid, formic acid, succinic acid, citric acid, malic acid, maleic acid, oxalic acid, or the like may be used only or two or more, but are not particularly limited thereto.

The weak acid may be used at a concentration of 0.5% (w/v) to 60% (w/v) in consideration of production costs and the separation of a salt produced after the neutralization of the weak acid. More particularly, the concentration of the weak acid may range from 20% (w/v) to 40% (w/v).

Agarooligosaccharides produced after the above pretreatment are allowed to react with an exo-type agarase, which produces disaccharides, to produce agarotriose and neoagarobiose.

The agarotriose is treated with an agarolytic β-galactosidase, which is an enzyme for decomposing the β-1,4 linkages of non-reducing ends of agarotriose, to produce 3,6-anhydro-L-galactose and neoagarobiose, and, finally, the neoagarobiose is decomposed into D-galactose and 3,6-anhydro-L-galactose, which are monosaccharides, using an α-neoagarobiose hydrolase.

The enzymatic reaction may be performed at a temperature of 20° C. to 40° C. for 30 min to 7 days.

The enzymatic reaction will be described in further detail as follows.

First, an enzyme that breaks a β-1,4-glycosidic linkage between D-galactose and 3,6-anhydro-L-galactose of agarose (hereinafter referred to as "Aga50D") may be used as the agarase that decomposes agarooligosaccharides to produce neoagarobiose which is a disaccharide.

The agarase includes not only an amino acid sequence set forth in SEQ ID NO: 1, but also proteins having an agarooligosaccharide-hydrolyzing activity as mutant proteins such as one or more substitutions, deletions, translocations, additions, or the like of the enzyme, which are within the scope of the enzyme of the present invention, and preferably includes an amino acid sequence with at least 80%, at least 85%, at least 90%, at least 93%, at least 94%, at least 95%, at least 96%, at least 97%, at least 98%, or at least 99% sequence homology to the amino acid sequence set forth in SEQ ID NO: 1.

The agarase may be derived from *Saccharophagus degradans* 2-40$^T$, but is not particularly limited thereto.

The agarase may be separated and purified from a supernatant of a culture of *Saccharophagus degradans* 2-40$^T$, and may be produced and separated: from strains other than *Saccharophagus degradans* using a genetic recombination technique; or by an artificial chemical synthesis method or the like.

When the recombination technique is used, factors used to facilitate the expression of typical recombinant proteins, for example, antibiotic-resistant genes, and reporter proteins or peptides usable in affinity column chromatography may be used, and such a technique falls within the scope which can be easily carried out by those skilled in the art to which the present invention pertains. For example, the agarase may be a culture supernatant of a transformant obtained through transformation of an edible strain, e.g., yeast. More detailed construct techniques may be found in Korean Patent Application Publication No. 2010-0040438 (published on Apr. 20, 2010).

A enzymatic hydrolysis reaction of agarooligosaccharides by using the agarase may be performed at a temperature of 20° C. to 40° C. for 30 minutes to 7 days. More particularly, the reaction there may be performed at a temperature of 25° C. to 35° C. for 1 day to 4 days.

Next, an agarolytic β-galactosidase (also referred to as "VejABG") that hydrolyzes agarotriose, which is an agarooligosaccharide hydrolysate into neoagarobiose and D-galactose, is effectively decomposes the agarotriose not hydrolyzed and remained by conventional method, and thus may significantly enhance the production efficiency of 3,6-anhydro-L-galactose from agarose.

The agarolytic β-galactosidase is an enzyme that belongs to the glycoside hydrolase (GH) family 2, and, when the activity thereof is compared with that of other β-galactosidases belonging to the GH family 2, the conventionally reported β-galactosidases do not exhibit the activity of producing D-galactose and neoagarobiose by decomposing agarotriose, but the agarolytic β-galactosidase derived from *Vibrio* sp. EJY3 may exhibit the lytic activity against agarotriose. In addition, the agarolytic β-galactosidase acts on non-reducing ends of various agarooligosaccharides (n), for example, agaropentaose and agaroheptaose, thereby hydrolyzing the agarooligosaccharides into D-galactose and neoagarobiose (n-1).

The agarolytic β-galactosidase may be transcribed and translated through a DNA fragment which is associated with the production of a polypeptide including regions upstream and downstream of a coding region of the enzyme and an intervening sequence between individual coding fragments, i.e., a coding gene. For example, the agarolytic β-galactosidase may be transcribed and translated from a sequence set forth in SEQ ID NO: 2, but is not particularly limited thereto. In addition, proteins having an agarotriose hydrolyzing activity as mutant proteins such as one or more substitutions, deletions, translocations, additions, or the like of the enzyme may also be within the scope of the enzyme of the present invention, and the enzyme preferably includes an amino acid sequence with at least 80%, at least 85%, at least 90%, at least 93%, at least 94%, at least 95%, at least 96%, at least 97%, at least 98%, or at least 99% sequence homology to the amino acid sequence set forth in SEQ ID NO: 2.

The agarolytic β-galactosidase may be separated and purified from a supernatant of a culture of *Vibrio* sp. EJY3, and may be produced and separated: from strains other than *Vibrio* sp. EJY3 using a genetic recombination technique; or by an artificial chemical synthesis method or the like. When the recombination technique is used, a culture supernatant or a supernatant of transformed *Escherichia coli* obtained through transformation of *E. coli* may be used, but is not particularly limited thereto. More detailed production techniques may be found in Korean Patent Application Publication No. 2015-0043040 (published on Apr. 22, 2015).

A reaction between the agarotriose and the agarolytic β-galactosidase may be performed at a temperature ranging from 20° C. to 40° C. for 30 minutes to 7 days. More particularly, the reaction may be performed at a temperature ranging from 25° C. to 35° C. for 1 day to 4 days.

The agarolytic β-galactosidase may exhibit an optimum agarolytic activity with respect to agarotriose at about 30° C. to about 40° C. and a pH of about 5 to about 9.6.

Lastly, an α-neoagarobiose hydrolase (also referred to as "SdNABH") capable of decomposing the neoagarobiose into 3,6-anhydro-L-galactose and D-galactose includes not only an amino acid sequence set forth in SEQ ID NO: 3, but also proteins having an agarotriose hydrolyzing activity as mutant proteins such as one or more substitutions, deletions, translocations, additions, or the like of the enzyme, which are within the scope of the enzyme of the prevent invention, and preferably includes an amino acid sequence with at least 80%, at least 85%, at least 90%, at least 93%, at least 94%, at least 95%, at least 96%, at least 97%, at least 98%, or at least 99% sequence homology to an amino acid sequence set forth in SEQ ID NO: 4.

The α-neoagarobiose hydrolase may be derived from *Saccharophagus degradans* 2-40$^T$, but is not particularly limited thereto.

The α-neoagarobiose hydrolase may be separated and purified from a culture supernatant or a supernatant of *Saccharophagus degradans* 2-40$^T$, and may be produced and separated: from strains other than *Saccharophagus degradans* using a genetic recombination technique; or by an artificial chemical synthesis method or the like. When the recombination technique is used, a culture supernatant or a supernatant of transformed *E. coli* obtained through transformation of *E. coli* may be used, but is not particularly limited thereto. More detailed production techniques may be found in Korean Patent Application Publication No. 2013-0085017 (published on Jul. 26, 2013).

A reaction between the neoagarobiose and the α-neoagarobiose hydrolase may be performed at a temperature ranging from 20° C. to 40° C. for 30 minutes to 7 days. More particularly, the reaction may be performed at a temperature ranging from 25° C. to 35° C. for 1 day to 4 days.

Silica gel chromatography, which is adsorption chromatography, and Bio-gel P2 chromatography, which is gel permeation chromatography, may be sequentially performed on decomposition products of the neoagarobiose, thereby separating and purifying 3,6-anhydro-L-galactose with a high purity of approximately 95%.

In the present specification, the terms "protein" and "polypeptide" may be used interchangeably.

In the present invention, a polypeptide having a sequence homology of a certain percentage (for example, 80%, 85%, 90%, 95%, or 99%) with respect to another sequence means that two sequences has the same amino acid residues at the above percentage upon sequence comparison when the two sequences are aligned with respect to each other. The alignment and percentage homology or identity may be determined using any suitable software program known in the related art, for example, those described in Current Protocols in Molecular Biology (F. M. Ausubel, et al., (eds) 1987 Supplement 30 section 7.7.18). A preferred program includes GCG Pileup programs, for example, FASTA (Pearson, et al., 1988 *Proc. Natl. Acad. Sci. USA* 85: 2444-2448), and BLAST (BLAST Manual, Altschul et al., Natl. Cent. Biotechnol. Inf., Natl Lib. Med. (NCIB NLM NIH), Bethesda, Md., and Altschul et al., 1997 NAR25: 3389-3402). Another preferred alignment program is ALIGN Plus (Scientific and Educational Software, PA), which preferably uses basic parameters. Still another preferred sequence software program which may be used herein is a TFASTA Data Searching program available in Sequence Software Package Version 6.0 (Genetics Computer Group, University of Wisconsin, Madison Wis.).

In the present invention, the term "recombination" used in connection with cells, nucleic acids, proteins, or vectors indicates that the cells, nucleic acids, proteins, or vectors are modified by introduction of heterologous nucleic acids or proteins or alteration of innate nucleic acids or proteins, or that the cells are derived from such modified cells. That is, the recombinant cells, for example, express genes which are not found in the cells in an original non-recombinant form, or express original genes which are expressed abnormally upon expression or not expressed at all.

In this specification, the term "nucleic acid" encompasses all types of single- or double-stranded DNAs, RNAs, and chemical variants thereof. The terms "nucleic acid" and "polynucleotide" may be used interchangeably herein. Since the genetic codes are degenerated, one or more codons may be used to encode a specific amino acid, and the present invention covers polynucleotides encoding certain amino acid sequences.

The term "introduction" used to describe an insertion of a nucleic acid sequence into cells refers to "transfection," "transformation," or "transduction," and encompasses references to the integration of a nucleic acid sequence into eukaryotic or prokaryotic cells. In this case, the nucleic acid sequence is integrated into the genome (for example, a chromosome, a plasmid, a plastid, or mitochondrial DNA) of a cell, and converted into an autonomous replicon or expressed temporally.

Silica gel chromatography, which is adsorption chromatography, and Bio-Gel P2 chromatography, which is gel permeation chromatography, may be used to separate and purify only 3,6-anhydro-L-galactose from reaction products obtained after the above-described enzymatic reaction, and 3,6-anhydro-L-galactose may be quantified by gas chromatography/mass spectrometry (GC/MS).

The pharmaceutical composition of the present invention may further include a pharmaceutically acceptable carrier.

The pharmaceutically acceptable carrier includes carriers and vehicles commonly used in the medical field, and examples thereof include, but are not limited to, ion exchange resins, alumina, aluminum stearate, lecithin, serum proteins (e.g., human serum albumin), buffer substances (e.g., phosphates, glycine, sorbic acid, potassium sorbate, and partial glyceride mixtures of saturated vegetable fatty acids), water, salts or electrolytes (e.g., protamine sulfate, disodium hydrogen phosphate, potassium hydrogen phosphate, sodium chloride, and zinc salts), colloidal silica, magnesium tri silicate, polyvinyl pyrrolidone, cellulose-based substrates, polyethylene glycol, sodium carboxymethylcellulose, polyarylate, waxes, polyethylene glycol, and wool fat.

In addition, the pharmaceutical composition of the present invention may further include, in addition to the above-described ingredients, a lubricant, a wetting agent, an emulsifying agent, a suspension agent, a preservative, or the like.

In one embodiment, the pharmaceutical composition according to the present invention may be formulated in the form of various preparations suitable for oral administration or parenteral administration.

Non-limiting examples of the preparations for oral administration include troches, lozenges, tablets, aqueous suspensions, oily suspensions, prepared powders, granules, emulsions, hard capsules, soft capsules, syrups, and elixirs.

To formulate the pharmaceutical composition of the present invention to be used for oral administration, a binder such as lactose, saccharose, sorbitol, mannitol, starch, amylopectin, cellulose, gelatin, or the like; an excipient such as dicalcium phosphate or the like; a disintegrating agent such as corn starch, sweet potato starch, or the like; a lubricant such as magnesium stearate, calcium stearate, sodium stearyl fumarate, polyethylene glycol wax, or the like; or the like may be used, and a sweetener, a fragrance, syrup, or the like may also be used.

Furthermore, in the case of capsules, in addition to the above-mentioned substances, liquid carriers such as fatty oils may be further used.

Non-limiting examples of the preparations for parenteral administration include injections, suppositories, respiratory inhalation powders, aerosols for spray, oral sprays, oral cleansers, toothpastes, ointments, powder for application, oils, and creams.

To formulate the pharmaceutical composition of the present invention to be used for parenteral administration, sterilized aqueous solutions, non-aqueous solvents, suspensions, emulsions, freeze-dried preparations, agents for external application, or the like may be used, and as the non-aqueous solvents and the suspensions, propylene glycol, polyethylene glycol, a vegetable oil such as olive oil, an injectable ester such as ethyloleate or the like may be used.

In addition, more particularly, when the pharmaceutical composition of the present invention is formulated as an injection, the composition of the present invention may be mixed in water with a stabilizer or a buffer to be prepared into a solution or a suspension, which is then formulated into a unit dosage form such as an ampoule or a vial. In addition, when the pharmaceutical composition of the present invention is formulated as an aerosol, a propellant or the like may be mixed with an additive to disperse a water-dispersed concentrate or wet powder.

In addition, when the pharmaceutical composition of the present invention is formulated as an ointment, a cream, or the like, the pharmaceutical composition may be formulated using a carrier such as an animal oil, a vegetable oil, wax, paraffin, starch, tragacanth, cellulose derivatives, polyethylene glycol, silicone, bentonite, silica, talc, zinc oxide, or the like.

A pharmaceutically effective amount and an effective dose of the pharmaceutical position of the present invention may vary depending on the formulation method, administration manner, administration schedule and/or administration route, or the like, and may vary according to various factors including the type and degree of the reaction to be achieved via administration of the pharmaceutical composition, the type of individual to which the composition is administrated, age, body weight, general health conditions, the symptoms or severity of diseases, gender, diet, excretion, drugs used simultaneously or at different times in the corresponding individual, ingredients of other compositions, and the like and similar factors well known in the medical field. The effective dose may be easily determined and prescribed for desired treatment by those of ordinary skill in the art. The pharmaceutical composition of the present invention may be administered once or several times a day. Thus, the dose is not intended to limit the scope of the present invention in any way.

The administration route and administration manner of the pharmaceutical composition of the present invention may be independent from each other, the administration method is not particularly limited, and the administration route and the administration manner may be an arbitrary administration route and administration route as long as they enable the pharmaceutical composition to reach the corresponding site. The pharmaceutical composition may be administered orally or parenterally.

The parenteral administration may be, for example, intravenous administration, intraperitoneal administration, intramuscular administration, transdermal administration, subcutaneous administration, or the like, and the composition may be applied or sprayed on a disease site, or inhaled, but are not limited thereto.

The pharmaceutical composition of the present invention may preferably be administered orally or via injection.

The term "prevention" as used herein means all actions that inhibit or delay the onset of an oral disease via administration of the pharmaceutical composition of the present invention to an individual.

The term "treatment" as used herein means all actions that alleviate or beneficially change symptoms of an oral disease via administration of the pharmaceutical composition of the present invention to an individual.

In the present invention, the oral disease is a concept encompassing all diseases occurring in the oral cavity regardless of symptoms thereof, and may include, for example, oral diseases mainly derived from oral microorganisms such as *Streptococcus mutans, Streptococcus oralis, Streptococcus sanguinis, Fusobacterium nulcleatum, Porphyromonas gingivalis, Actinomyces viscosus, Actinobacillus actinomycetemcomitans, Candida albicans*, and the like, or oral diseases caused by oral immunity degradation. Non-limiting examples of the oral disease include dental caries, gingivitis, periodontitis, oral mucous ulcer, halitosis, and xerostomia.

The present invention also provides a method of treating an oral disease, including administering a pharmaceutically effective amount of the pharmaceutical composition for preventing or treating an oral disease to a subject in need thereof.

As used herein, the term "subject" includes all animals including mammals including mice, livestock, humans, and the like.

In the method of treating an oral disease of the present invention, the description of dosage, administration route, administration manner, and the like of the pharmaceutical composition is the same as described above in connection with the pharmaceutical composition of the present invention.

The term "effective amount" refers to an amount required to at least partially achieve desired immune responses or delay or completely stop the onset or progression of specific diseases to be treated. The amount varies according to health and physical conditions of a subject to be treated, the classification group of a subject to be treated, the ability of an immune system of a subject to synthesize an antibody, the degree of desired protection, vaccine preparations, evaluation of medical conditions, and other related factors. The amount will be within a relatively broad range measurable through general attempts.

The present invention also relates to an oral hygienic composition for preventing or alleviating an oral disease, which includes 3,6-anhydro-L-galactose.

In the present invention, the description of the 3,6-anhydro-L-galactose, oral disease, and prevention is the same as described above in connection with the pharmaceutical composition of the present invention.

In the present invention, the oral hygienic composition includes all types and preparations that may be used for hygiene of the oral cavity. For example, the oral hygienic composition may be included in an oral product selected from the group consisting of a toothpaste, an oral cleanser, a mouthwash, an oral spray, an oral ointment, an oral varnish, an oral gargle, and gum.

The oral hygienic composition of the present invention may be formulated in the form of various preparations suitable for oral administration or parenteral administration to be used, and description related thereto is the same as described above in connection with the pharmaceutical composition of the present invention.

The term "alleviation" as used herein means all actions that decrease at least the degree of parameters related to conditions being treated, e.g., symptoms.

The present invention also relates to a food composition for preventing or alleviating an oral disease, which includes 3,6-anhydro-L-galactose.

In the present invention, the description of the 3,6-anhydro-L-galactose, oral disease, prevention, and alleviation is the same as described above in connection with the pharmaceutical composition of the present invention.

The food composition of the present invention is not particularly limited, and includes a health functional food composition.

The term "health functional food" refers to a food prepared by adding the 3,6-anhydro-L-galactose to food substances such as beverages, teas, condiments, gums, confectionaries, or the like, or a food prepared in the form of capsules, powder, suspensions, or the like, and refers to a food that imparts a specific health effect when ingested.

When the health functional food composition of the present invention is used as a food additive, the composition may be directly added or may be used in combination with other foods or food ingredients, and may be appropriately used according to a general method.

The type of the food is not particularly limited, and includes all foods in a usual sense. Non-limiting examples of foods to which the material is applicable include meat, sausages, bread, chocolates, candies, snacks, confectionaries, pizza, ramen, other noodles, gums, dairy products including ice creams, various soups, beverages, teas, drinks, alcoholic beverages, and vitamin complexes.

When the health functional food composition of the present invention is a beverage composition, the beverage composition may include various flavor enhancers, natural carbohydrates, or the like as additional ingredients like general beverages. Non-limiting examples of the natural carbohydrates include monosaccharides such as glucose and fructose; disaccharides such as maltose and sucrose; natural sweeteners such as dextrin and cyclodextrin; and synthetic sweeteners such as saccharin and aspartame. A ratio of the added additional ingredients may be appropriately selected and determined by those of ordinary skill in the art.

In addition, the health functional food composition of the present invention may include various nutrients, vitamins, electrolytes, a flavoring agent, a colorant, pectic acid and a salt thereof, alginic acid and a salt thereof, organic acids, a protective colloidal thickening agent, a pH adjusting agent, a stabilizer, a preservative, glycerin, alcohols, carbonating agents used in carbonated beverages, or the like. In addition, the health functional food composition of the present invention may include pulp for preparing natural fruit juices, fruit beverages, vegetable beverages, or the like. These ingredients may be used alone or a combination of two or more of these ingredients may be used. A ratio of these additives may also be appropriately selected by those of ordinary skill in the art.

Hereinafter, the present invention will be described in detail with reference to the following examples. These examples are provided for illustrative purposes only and are not intended to limit the scope of the present invention.

<Example 1> Pretreatment of Agarose

Agarose was dissolved in 3N acetic acid to a concentration of 7% (w/v) to allow a reaction to occur there between using a microwave digester at 130° C. for 10 minutes, and then the reaction product was washed twice with 1.5 L of 94% ethanol to remove the residual acetic acid and an excessive decomposition product. The reaction product was freeze-dried for 24 hours to obtain a powder-type agarooligosaccharide.

<Example 2> Production of 3,6-anhydro-L-galactose by Enzymatic Hydrolysis of Agarooligosaccharide The acid hydrolysate (agarooligosaccharide) produced in Example 1 was allowed to react with an exo-type β-agarase, i.e., Aga50D (see Korean Patent Application Publication No. 2010-0040438, published on Apr. 20, 2010) to be decomposed into D-galactose and 3,6-anhydro-L-galactose, which are monosaccharides, and agarotriose and neoagarobiose were produced as reaction products.

After the Aga50D reaction was completed, the agarotriose was treated with enzyme VejABG (see Korean Patent Application Publication No. 2015-0043040, published on 22 Apr. 2015), which is an enzyme that decomposes β-1,4 linkages of non-reducing ends, to produce 3,6-anhydro-L-galactose and neoagarobiose.

To produce D-galactose and 3,6-anhydro-L-galactose, which are monosaccharides from the neoagarobiose, the reaction product of VejABG was reacted with the SdNABH enzyme (see Korean Patent Application Publication No. 2013-0085017, published on Jul. 26, 2013).

The three recombinant enzymes were expressed in *Escherichia coli* BL21(DE3) and purified with a HisTrap column. The enzymatic reaction was performed by adding 5% (w/v) of agarooligosaccharide to 200 mL of a 50 mM Tris-HCl buffer (pH 7.4) and allowing the resulting solution to sequentially react with Aga50D, VejABG, and SdNABH at 30° C. for 3 days. The enzymes, i.e., Aga50D, VejABG, and SdNABH were used in the enzymatic reaction in amounts of 20 mg, 1 mg, and 2 mg, respectively, with respect to a total amount of 200 mL.

<Example 3> Separation and Purification Using Silica Gel Chromatography and Bio-Gel P2 Chromatography Chromatography was performed to separate and purify only 3,6-anhydro-L-galactose from the reaction products produced in Example 2. The reaction products were adsorbed onto Celite to form a sample in the form of powder, and then subjected to silica gel chromatography, which is adsorption chromatography. A solvent obtained by mixing chloroform, methanol, and water at a ratio of 78:20:2 (v/v/v) was used as a mobile phase, and the total volume of the solvent as the mobile phase was 4 L. The volume of one fraction was 20 mL, and the sample consisting of a total of 200 fractions was analyzed through TLC, and thus among these, the fractions containing 3,6-anhydro-L-galactose were collected and the organic solvent was removed therefrom using a rotary vacuum concentrator.

<Example 4> Qualification and Quantification of 3,6-Anhydro-L-Galactose Using GC/MS Analysis The high-purity 3,6-anhydro-L-galactose produced in Example 3 was quantified through GC/MS analysis. A derivatization procedure for GC/MS analysis was as follows. The purified sample was dried in a vacuum concentrator, added to 10 μl of 4% (w/v) O-methylhydroxylamine hydrochloride in pyridine, and then reacted at 30° C. for 120 min. Then, 45 μl of N-methyl-N-(trimethylsilyl)trifluoroacetamide was added to the resulting product, and reacted at 37° C. for 30 minutes. The equipment conditions for GC/MS analysis were as follows. A column used for analysis was a DB5-MS capillary column. In the case of the GC column temperature conditions, first, the sample was maintained at a temperature of 100° C. for 3.5 min, heated to 160° C., and maintained for 20 min. Thereafter, the sample was heated to 200° C., maintained for 15 min, finally heated to 280° C., and maintained for 5 min. One microliter of the sample was analyzed at a split ratio of 9.6.

<Example 5> Cell Culture Conditions

Strains used in the present experiment are *Streptococcus mutans* ATCC 25175, *S. oralis*, and *S. sanguinis*. Representatively, *Streptococcus mutans* ATCC 25175 was pre-cultured in a brain-heart infusion (BHI) medium for 12 hours, and was washed twice with a 2 mM potassium phosphate buffer, and then was subjected to main culture in a minimal medium prepared with reference to the previously reported document (Fujiwara et al (1978) Arch Oral Biol. 23, 601-602) at 37° C. and 180 rpm. The composition of the minimal medium includes, in 5 mL of a 50 mM Tris-HCl buffer (pH 7.4), 10 mg of L-glutamic acid, 1 mg of cysteine hydrochloride, 4.5 mg of L-leucine, 5 mg of ammonium chloride, 17.5 mg of potassium hydrogen phosphate, 7.5 mg of potassium dihydrogen phosphate, 21 mg of a carbonate, 6 mg of magnesium sulfate heptahydrate, 0.1 mg of manganese chloride tetrahydrate, 3 mg of sodium pyruvate, 5 μg of riboflavin, 2.5 μg of thiamine hydrochloride, 0.5 μg of biotin, 5 μg of nicotinic acid, 0.5 μg of p-aminobenzoic acid, 2.5 μg of calcium pantothenate, and 5 μg of pyridoxine hydrochloride.

<Example 6> Inhibitory Effect on the Growth of *Streptococcus mutans* Under the Single Carbon Source Condition To verify an effect of inhibiting the growth of *Streptococcus mutans* under a single carbon source condition, *Streptococcus mutans* was cultured in a solid minimal medium and a liquid minimal medium that contained 10 g/L of each of 3,6-anhydro-L-galactose, glucose, and xylitol. Pre-cultured *Streptococcus mutans* was diluted 10 fold, $10^2$ fold, $10^3$ fold, $10^4$ fold, or $10^5$ fold in a 2 mM potassium phosphate buffer, followed by spotting in a solid medium and cultivating for 30 h.

As shown in FIG. 1, the formation of colonies was inhibited under conditions of 3,6-anhydro-L-galactose and glucose compared to the glucose condition. In particular, in the case of 3,6-anhydro-L-galactose, colonies were not observed at all under $10^4$-fold and $10^5$-fold dilution conditions.

In addition, an effect of inhibiting cell growth was observed by culturing *Streptococcus mutans* in a liquid minimal medium containing 10 g/L of each carbon source (3,6-anhydro-L-galactose, glucose, and xylitol). The bacteria were main-cultured using the method of Example 5 for 35 h, and a degree of the cell growth was measured by measuring the absorbance of a culture at a wavelength of 600 nm every 5 h.

Figure 2:
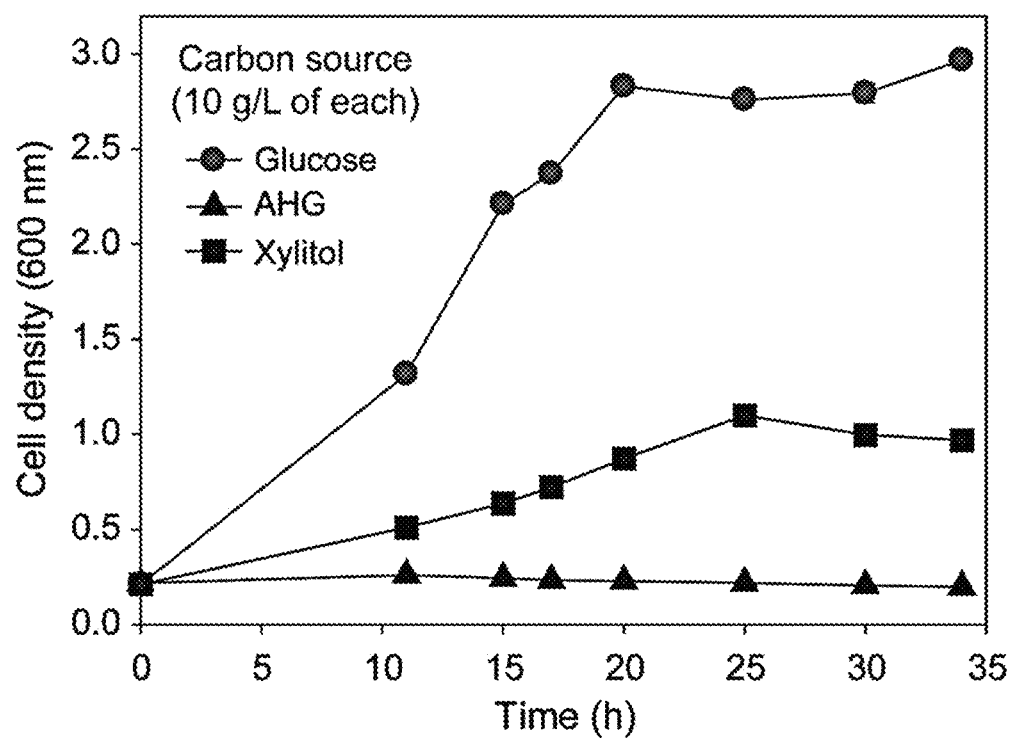
FIG. 2 illustrates an effect of a single carbon source on the growth of *Streptococcus mutans* in a liquid minimal medium supplemented with each of 10 g/L of glucose, 10 g/L of 3,6-anhydro-L-galactose, and 10 g/L of xylitol as carbon sources.

As shown in FIG. 2, under the glucose condition, a dry cell weight (DCW) of *Streptococcus mutans* was measured as a concentration of 4.05 g/L 20 h after entering a stationary phase, and in the case of xylitol, the dry cell weight (DCW) thereof was significantly decreased and measured as a concentration of 1.46 g/L, and in the case of 3,6-anhydro-L-galactose, the growth of *Streptococcus mutans* was not observed at all. Thus, it was confirmed that 3,6-anhydro-L-galactose is a non-fermentable sugar for *Streptococcus mutans* like xylitol, and had a much stronger growth inhibitory effect than xylitol.

<Example 7> Effect of Inhibiting Growth of *Streptococcus mutans* Under the Mixed Carbon Source Condition Small amounts of *Streptococcus mutans*, *S. oralis*, and *S. sanguinis* were cultured, using the method of Example 5, in 200 μl of a liquid minimal medium containing 10 g/L of glucose and 3,6-anhydro-L-galactose or xylitol according to concentration in a 96-well plate, and growth inhibitory effects thereof were observed by measuring absorbance at a wavelength of 600 nm according to time. The treated concentration of 3,6-anhydro-L-galactose was between 0 g/L and 20 g/L, and the treated concentration of xylitol was between 0 g/L and 60 g/L.

Figure 3A:
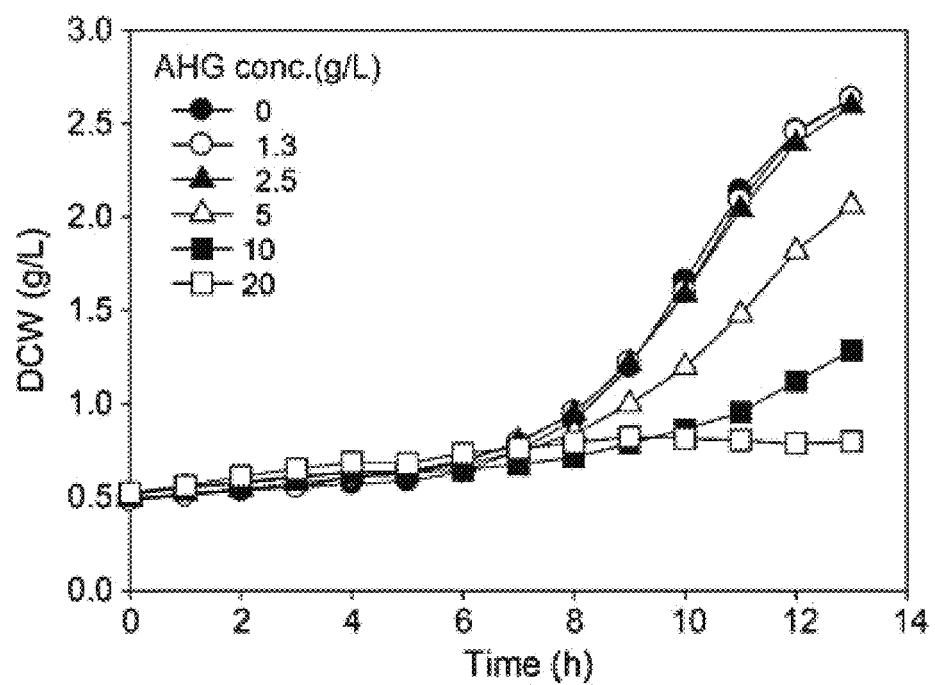
FIGS. 3*a*, 3*b*, 3*c*, 3*d*, 3*e* and 3*f* illustrate inhibitory effects of different concentrations of 3,6-anhydro-L-galactose (FIG. 3*a*) and xylitol (FIG. 3*b*) against *Streptococcus mutans* in a minimal medium containing 10 g/L of glucose as a carbon source, and concentration-dependent inhibitory effects against *S. oralis* (FIG. 3*c*: 3,6-anhydro-L-galactose, FIG. 3*d*: xylitol) and *S. sanguinis* (FIG. 3*e*: 3,6-anhydro-L-galactose, FIG. 3*f*: xylitol).
Figure 3B:
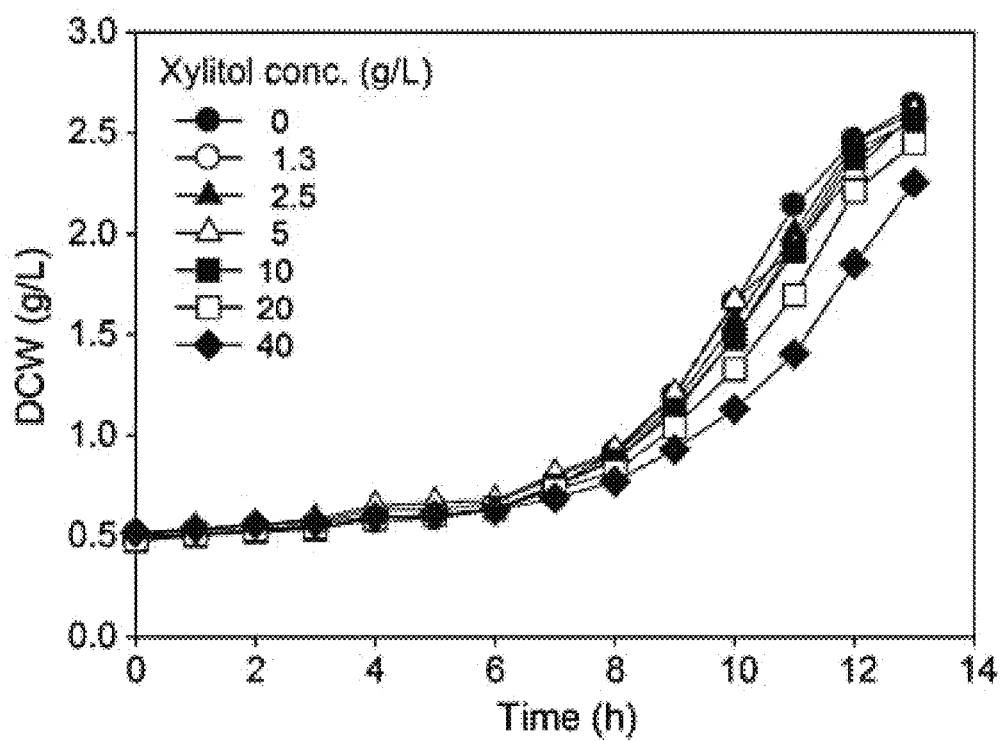

As shown in FIGS. 3a and 3b, there was no significant change in the growth of *Streptococcus mutans* at 1.3 g/L and 2.5 g/L of 3,6-anhydro-L-galactose, a considerable cell growth inhibitory effect was observed at 5 g/L and 10 g/L of 3,6-anhydro-L-galactose, and cell growth did not occur at 20 g/L of 3,6-anhydro-L-galactose. In the case of xylitol, the growth of *Streptococcus mutans* was inhibited as the treated concentration of xylitol was increased, but considerable cell growth was observed even at a significantly high concentration, i.e., 40 g/L. Thus, it was confirmed that 3,6-anhydro-L-galactose had a stronger cell growth inhibitory effect even at a lower concentration than xylitol.

Figure 3C:
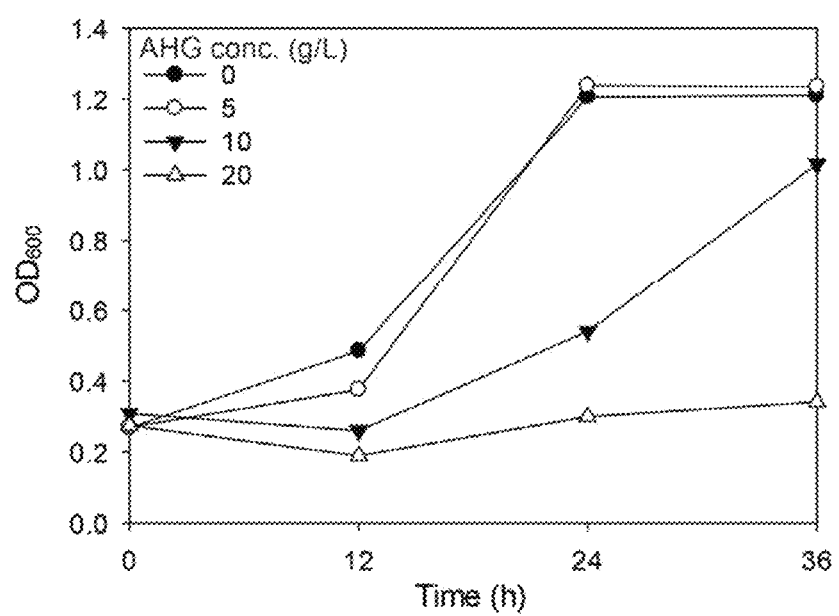
Figure 3D:
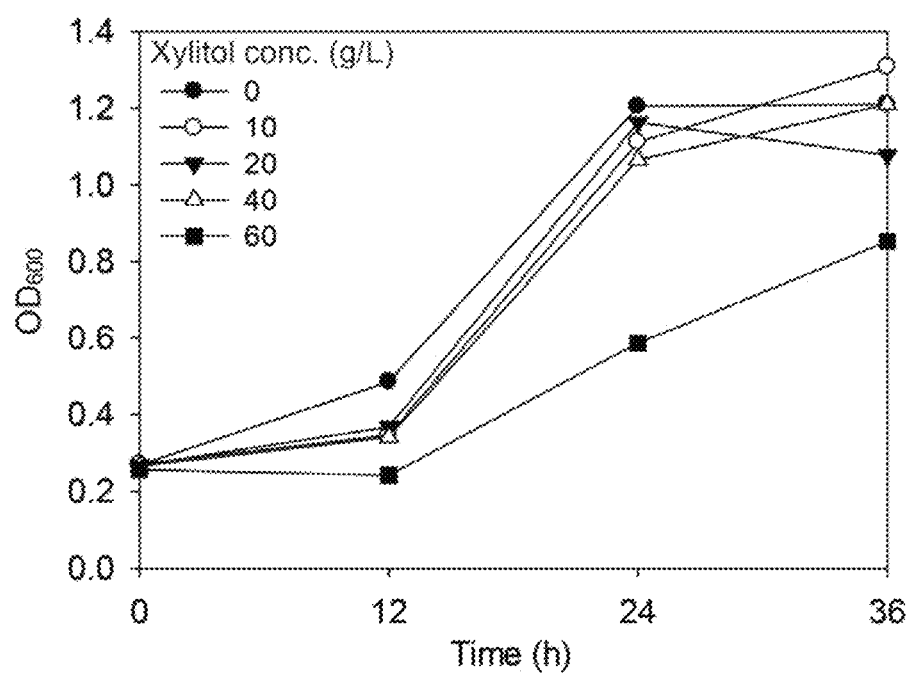
Figure 3E:
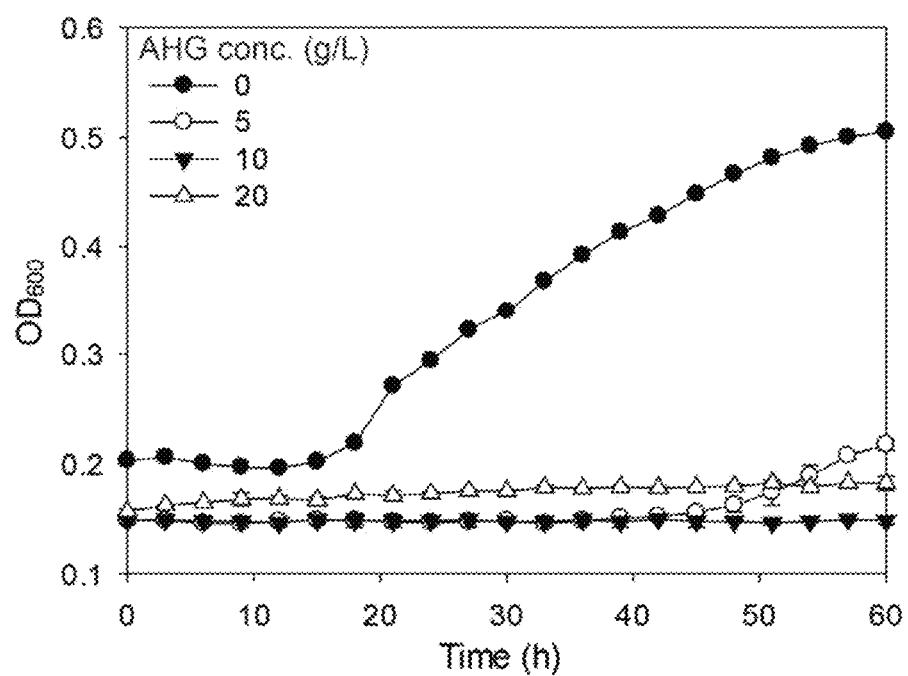
Figure 3F:
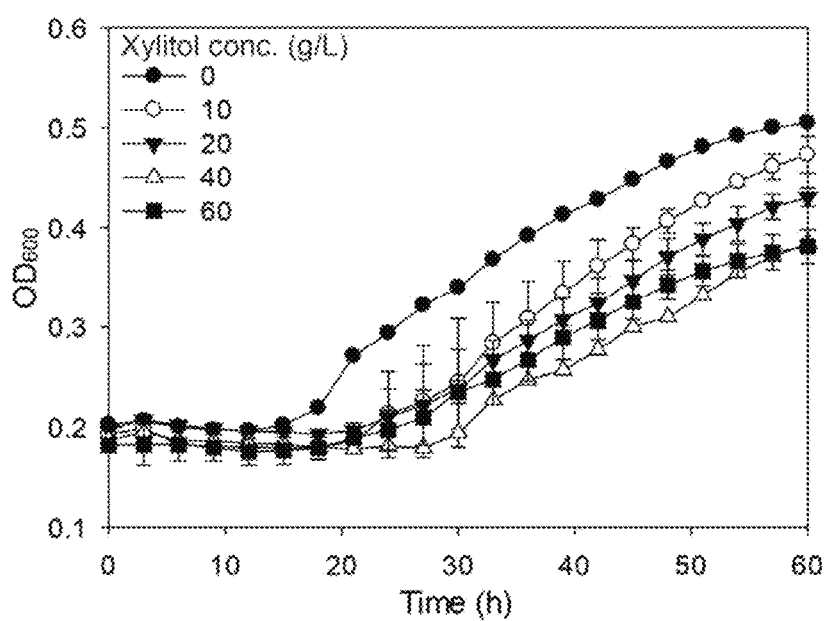

In addition, even with respect to *S. oralis* and *S. sanguinis*, 3,6-anhydro-L-galactose exhibited a greater cell growth inhibitory effect as the concentration thereof was increased (see FIGS. 3c and 3d). Xylitol exhibited a strong inhibitory effect on *S. sanguinis* at a high concentration, i.e., 60 g/L, of xylitol (see FIGS. 3e and 3f).

<Example 8> Effect of Inhibiting Growth of *Streptococcus mutans* and Acid Production Under the Mixed Carbon Source Condition To verify an effect of 3,6-anhydro-L-galactose or xylitol on the growth of *Streptococcus mutans* and acid production, *Streptococcus mutans* bacteria were cultured, using the method of Example 5, in 5 mL of a liquid minimal medium containing 10 g/L of glucose and 0 g/L, 5 g/L or 10 g/L of 3,6-anhydro-L-galactose or 20 g/L or 40 g/L of xylitol for 35 h, and cell growth was measured using absorbance every 5 hours and concentrations of an extracellular substrate and acid production were measured by HPLC. A glucose only-added condition was set as a negative control, and a glucose- and xylitol-added condition was set as a positive control. A column used for analysis was Aminex HPX-87H, and 0.01 N of sulfuric acid as a mobile phase was flowed at a rate of 0.5 mL/min and 65° C.

Figure 4A:
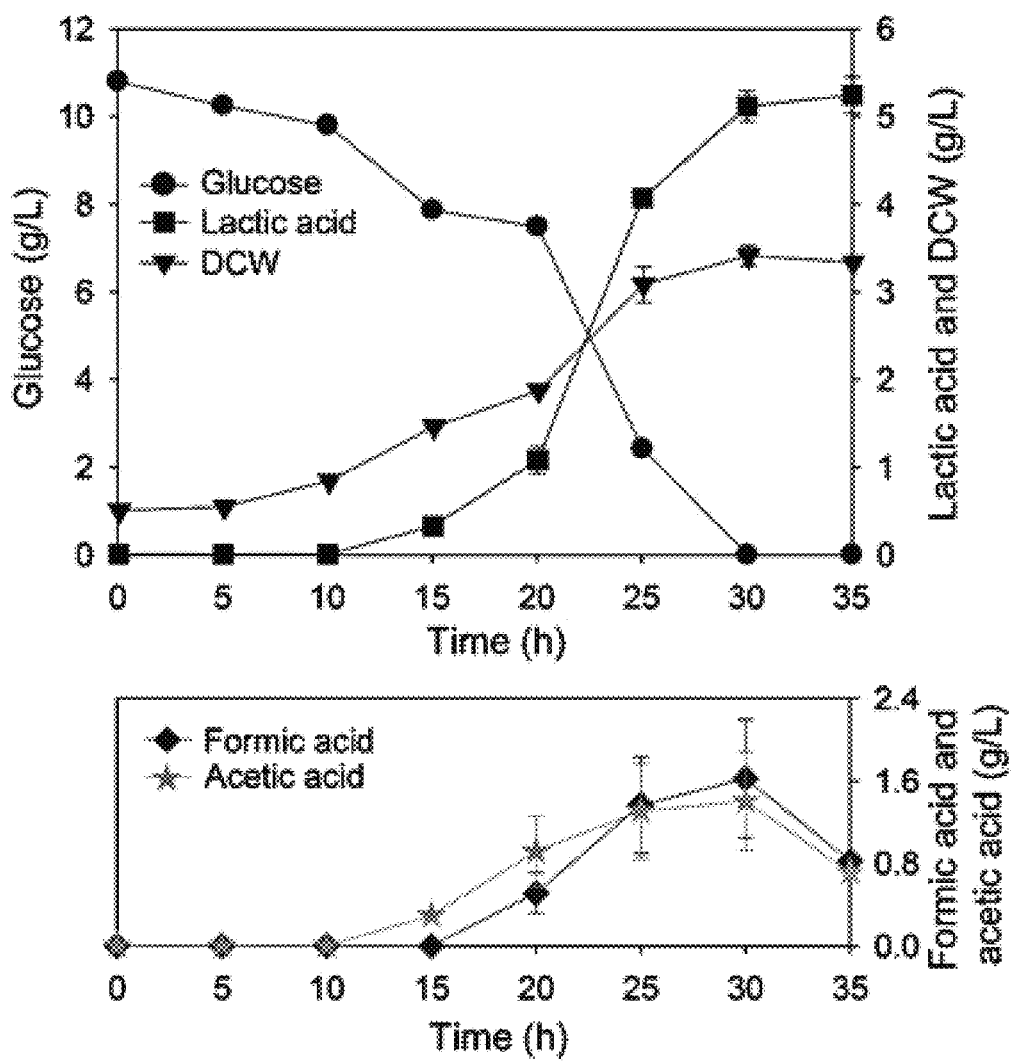
FIGS. 4*a*, 4*b* and 4*c* illustrate analysis results of the growth of *Streptococcus mutans*, the concentration of a remaining carbon source, and the amount of produced acid (lactic acid, formic acid, and acetic acid), in a minimal medium containing 10 g/L of glucose as a carbon source supplemented with each of 0 g/L (FIG. 4*a*), 5 g/L (FIG. 4*b*), and 10 g/L (FIG. 4*c*) of 3,6-anhydro-L-galactose.

As illustrated in FIG. 4a, under a condition of only glucose included as a carbon source, the dry cell weight was measured to be 3.34 g/L, and a non-growth rate was 0.086 $h^{-1}$. Glucose was all consumed in 30 hours and the concentration of lactic acid was measured as 5.24 g/L. In addition, the concentrations of formic acid and acetic acid produced in small amounts were 0.82 g/L and 0.71 g/L, respectively.

Figure 4B:
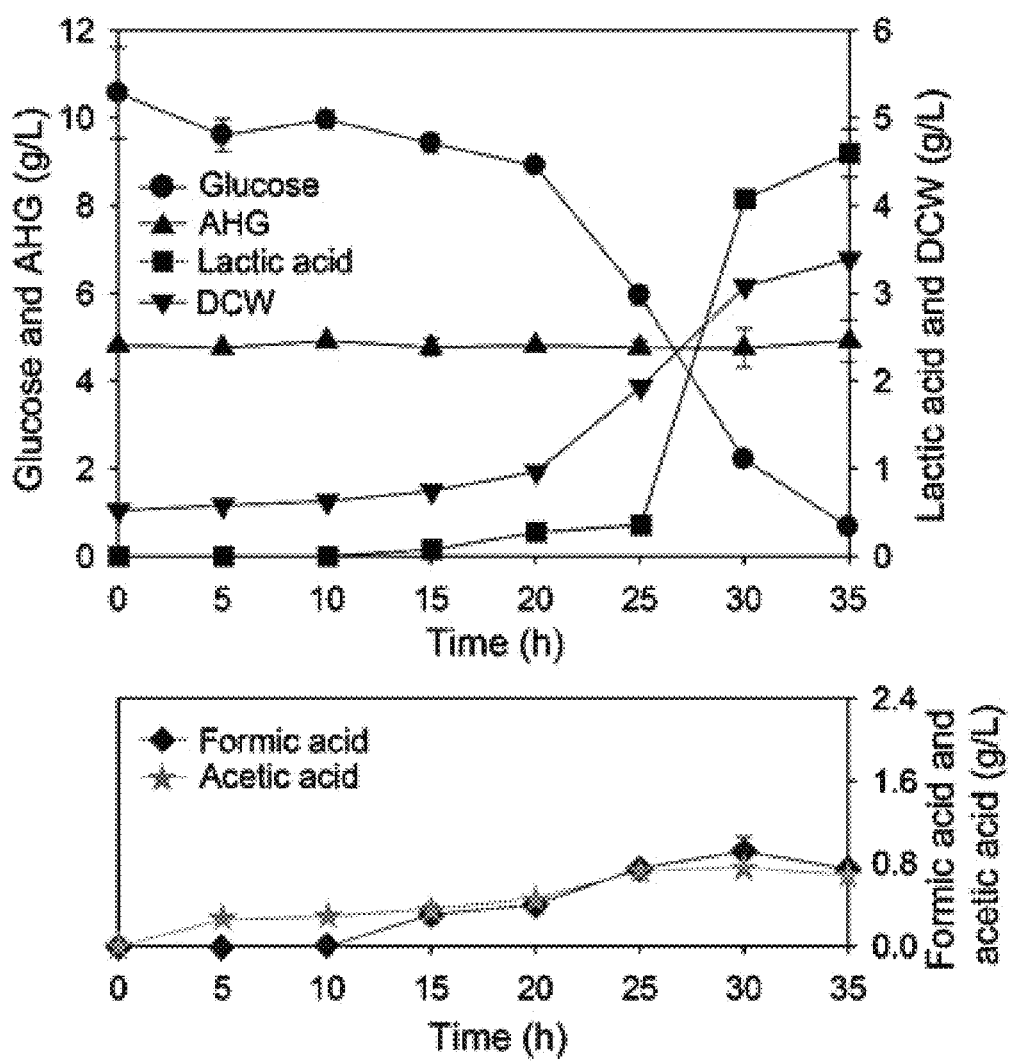

Under a condition of including 5 g/L of 3,6-anhydro-L-galactose in 10 g/L of glucose, there was no concentration decrease in a final dry cell weight of *Streptococcus mutans*, but the lag phase thereof was increased. From the results, i.e., a decrease in the non-growth rate to 0.075 $h^{-1}$ and a decrease in the concentration of produced acid, it was confirmed that the mixed carbon source had a weak effect of inhibiting cell growth and acid production (see FIG. 4b).

Figure 4C:
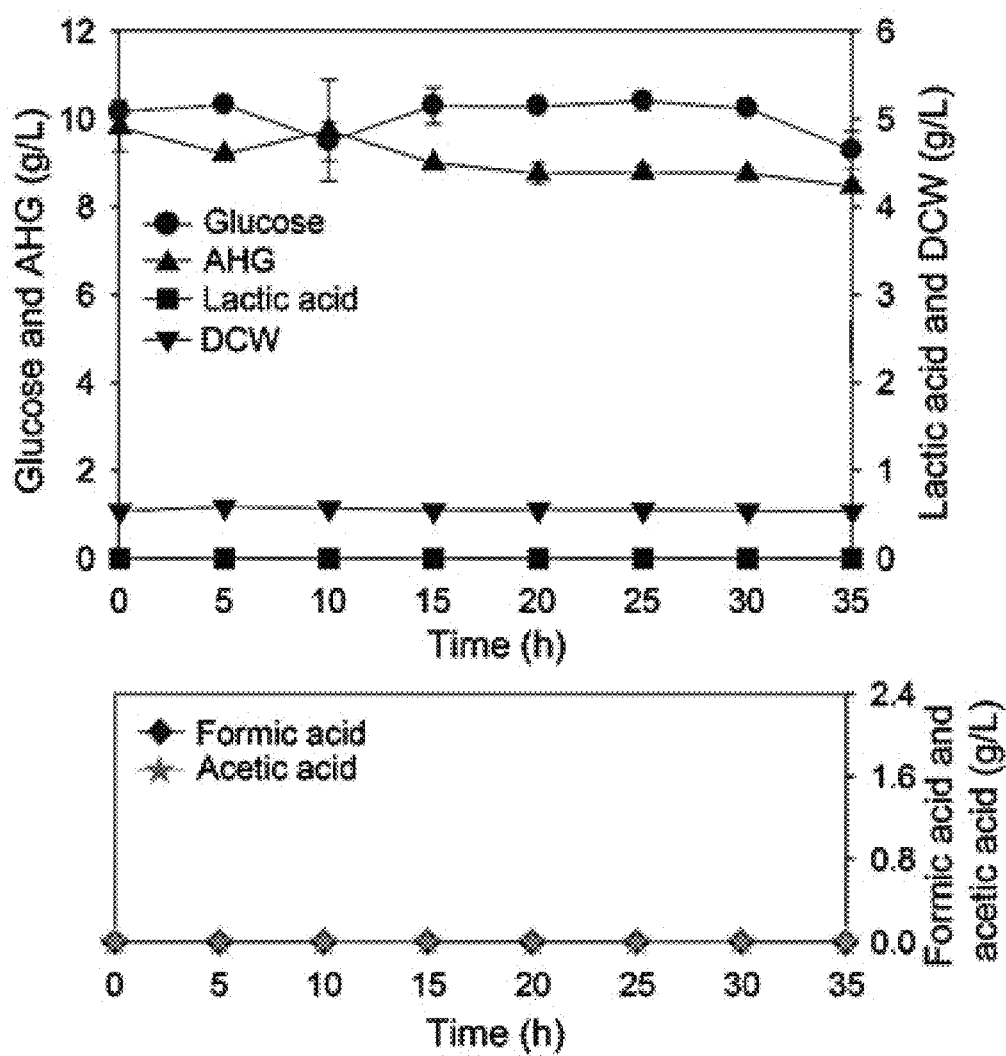

Under a condition of including 10 g/L of 3,6-anhydro-L-galactose in 10 g/L of glucose, the growth of *Streptococcus mutans* and acid production were not observed at all. In addition, under both conditions, there was no change in the concentration of 3,6-anhydro-L-galactose, from which it was confirmed that *Streptococcus mutans* was unable to use 3,6-anhydro-L-galactose as a carbon source (see FIG. 4c).

Figure 5A:
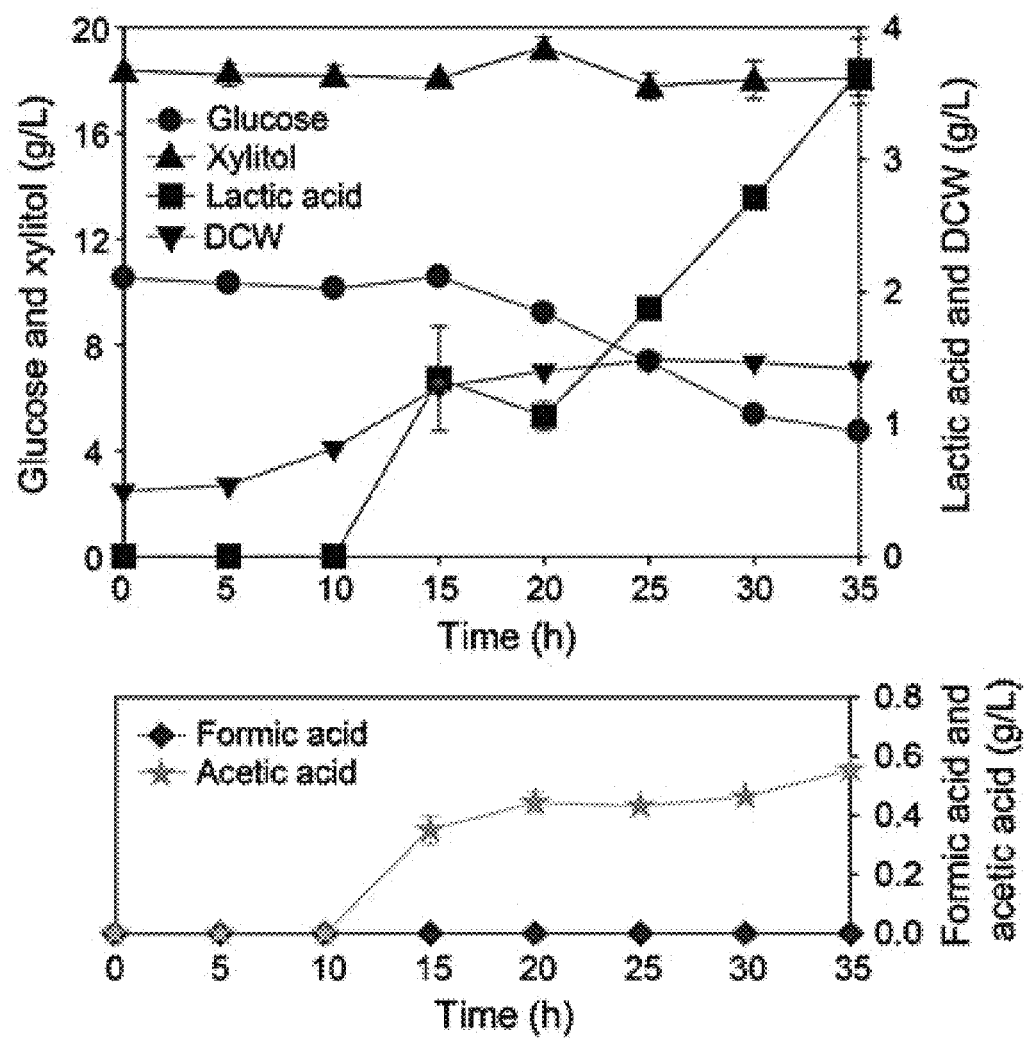
FIGS. 5*a* and 5*b* illustrate analysis results of the growth of *Streptococcus mutans*, the concentration of remaining carbon source, and the amount of produced acid (lactic acid, formic acid, and acetic acid), in a minimal medium containing 10 g/L of glucose as a carbon source supplemented with each of 20 g/L (FIG. 5*a*) and 40 g/L (FIG. 5*b*) of xylitol.
Figure 5B:
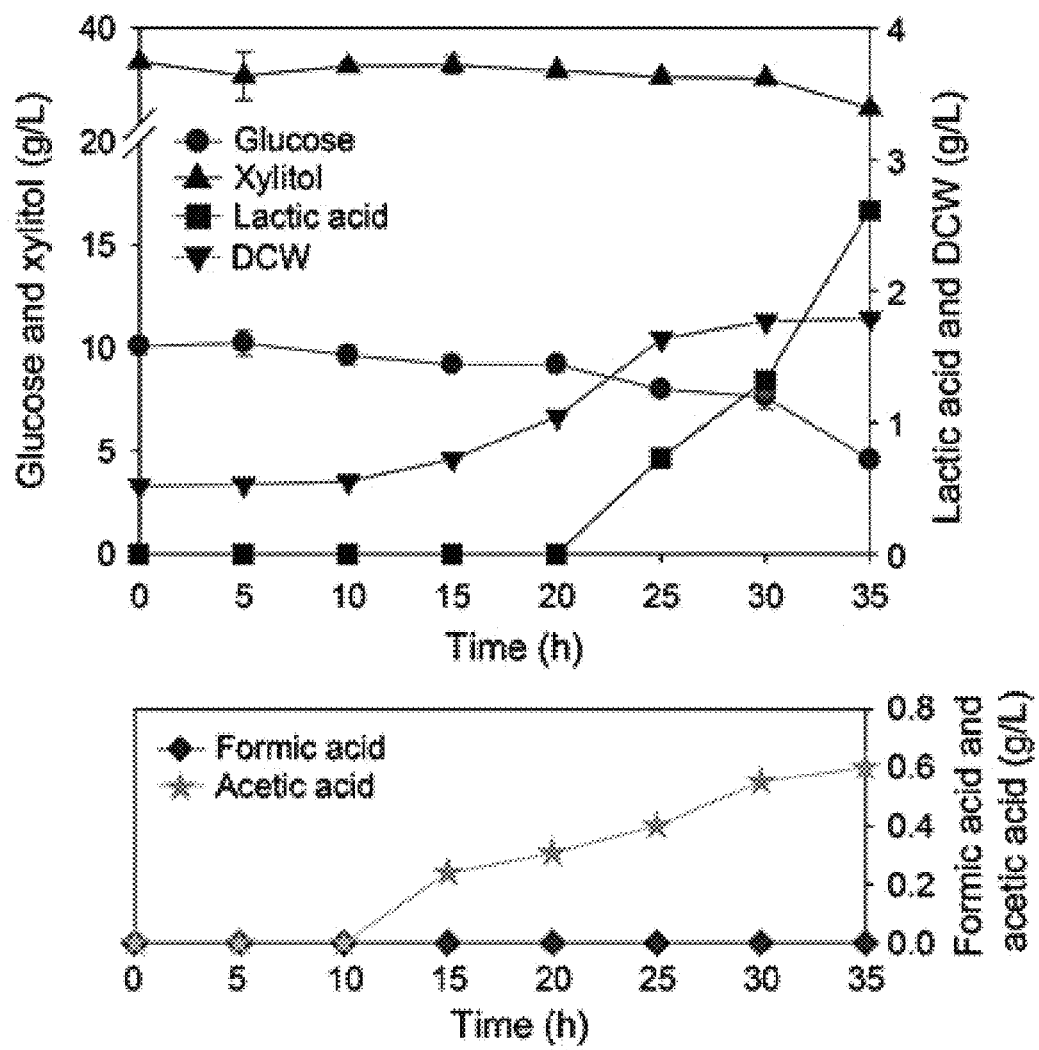

In addition, under a condition of including 20 g/L of xylitol in 10 g/L of glucose, the final dry cell weight was 1.42 g/L which indicates the inhibition of the growth of *Streptococcus mutans*, but there was no change in the non-growth rate, i.e., 0.087 $h^{-1}$ when compared to a non-growth rate, i.e., 0.086 $h^{-1}$ of the negative control. A total of 5.28 g/L of glucose was consumed, and the concentrations of produced lactic acid and acetic acid were 3.67 g/L and 0.55 g/L, respectively, which were lower than that of the negative control (see FIG. 5a). Under a condition of being included at a high concentration, i.e., 40 g/L of xylitol in 10 g/L of glucose, a longer lag phase than that of 20 g/L of xylitol was observed, and the concentration of consumed glucose was similarly measured as 5.42 g/L. Due to the consumption of glucose, the concentrations of produced lactic acid and acetic acid were measured as 3.67 g/L and 0.55 g/L, respectively (see FIG. 5b).

In addition, the concentration of xylitol was constantly maintained during the fermentation of *Streptococcus mutans*, from which it was confirmed that xylitol exhibited non-fermentation properties with respect to *Streptococcus mutans*.

From these results, it was confirmed that xylitol known as a sugar that prevents dental caries did not completely inhibit the growth of *Streptococcus mutans* and acid production even at a much higher concentration, i.e., 40 g/L, than that of 3,6-anhydro-L-galactose as in the results of the condition of 10 g/L of 3,6-anhydro-L-galactose. This indicates that 3,6-anhydro-L-galactose has a much stronger effect of inhibiting the growth of *Streptococcus mutans* and acid production even at a lower concentration than that of xylitol.

<Example 9> Inhibitory Effects of AHG and Xylitol on *Streptococcus mutans* Under Various Conditions of Sugars Other than Glucose Under conditions of fermentable sugars other than glucose, for example, sucrose, fructose, and maltose, inhibitory effects of AHG and xylitol on *S. mutans* were investigated. An experiment was carried out in a 96-well plate containing 0 g/L to 10 g/L of AHG or 0 g/L to 40 g/L of xylitol in a specified minimal medium containing 10 g/L of each of sucrose, fructose, and maltose.

Under the conditions of sucrose, fructose, and maltose, the growth of *S. mutans* was inhibited by AHG. Under the sucrose condition, a significant decrease in cell growth was not observed in the case of 1.3 g/L of AHG, but the cell growth was significantly inhibited as the concentration of AHG was increased (2.5 g/L of AHG). The cell growth of *S. mutans* was completely inhibited at high concentrations, i.e., 5 g/L and 10 g/L of AHG (see FIG. 6a). Results similar to those for the inhibitory effect of AHG on the cell growth of *S. mutans* were observed even under the fructose and maltose conditions (see FIGS. 6b and 6c).

Figure 6A:
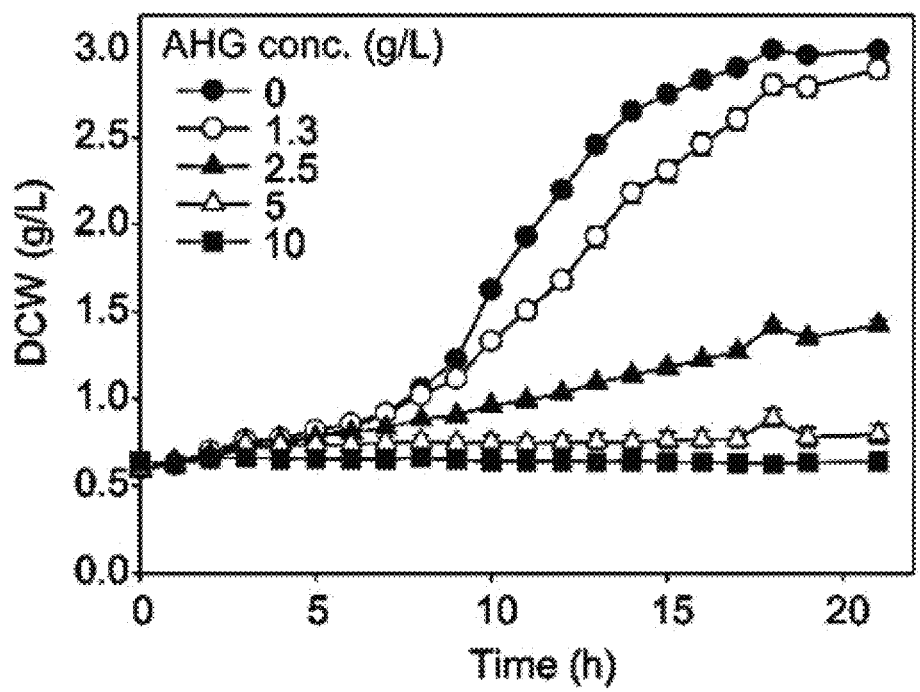
FIGS. 6*a*, 6*b*, 6*c*, 6*d*, 6*e* and 6*f* illustrate results of verifying the growth of *Streptococcus mutans* in a minimal medium containing 10 g/L of sucrose (FIGS. 6*a* and 6*d*), 10 g/L of fructose (FIGS. 6*b* and 6*e*), or 10 g/L of maltose (FIGS. 6*c* and 6*f*) as a carbon source supplemented with 3,6-anhydro-L-galactose (0-10 g/L.
Figure 6B:
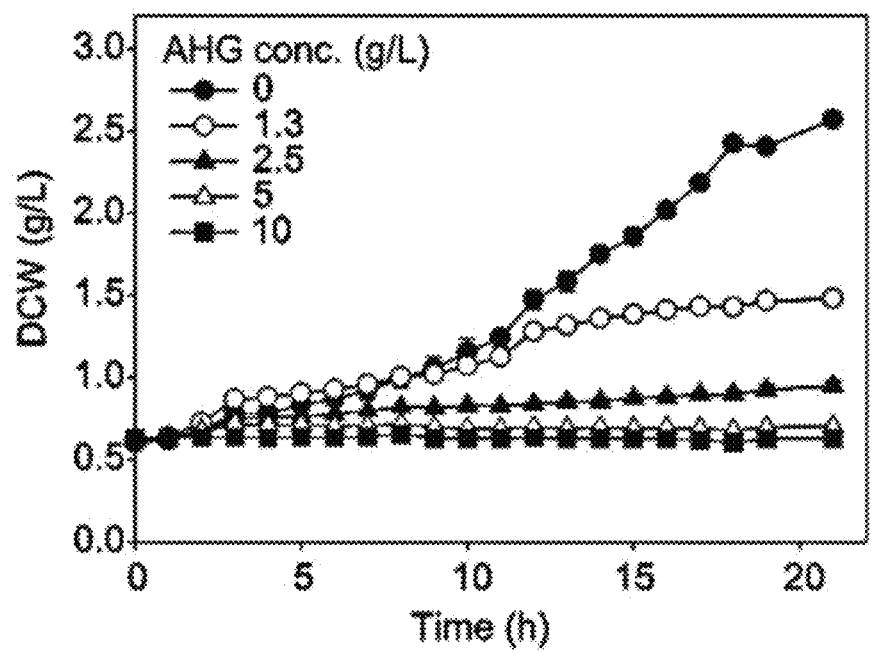
Figure 6C:
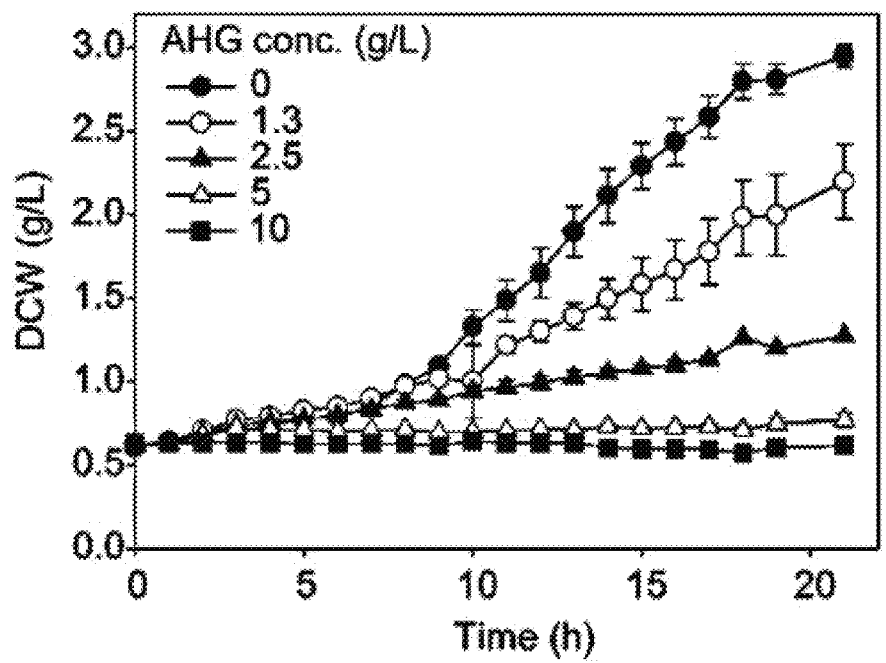
Figure 6D:
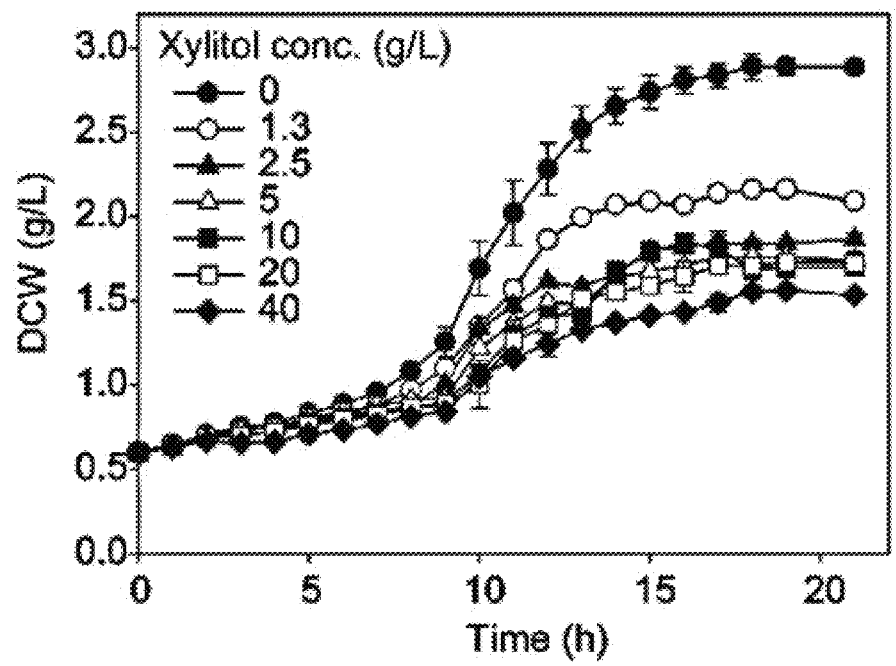
Figure 6E:
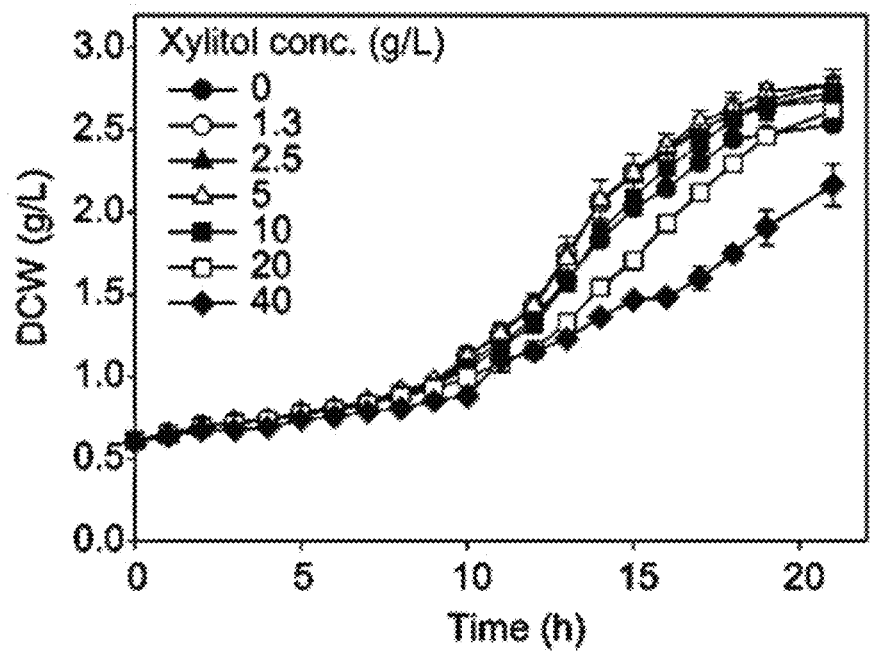
Figure 6F:
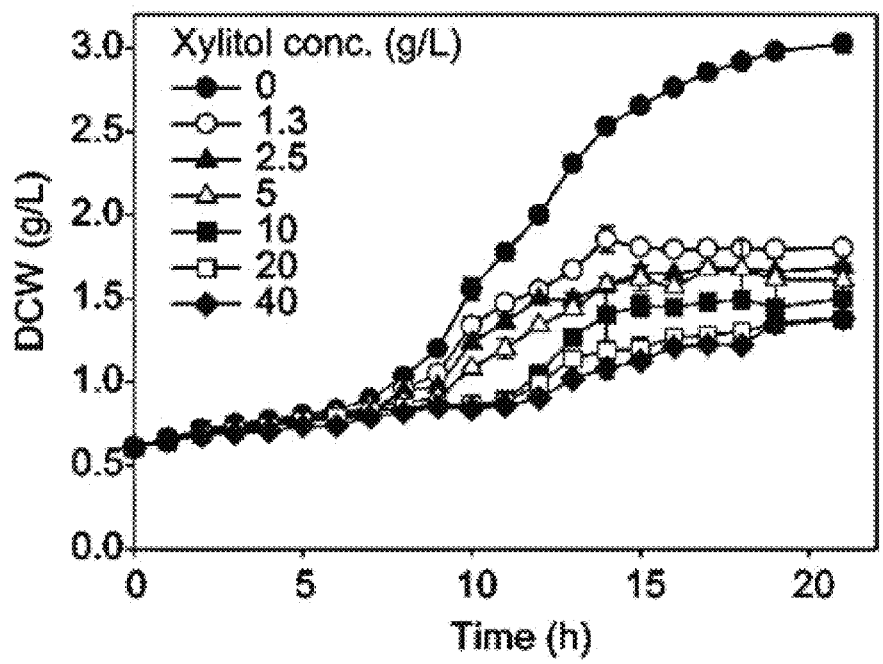

Under the condition of 2.5 g/L of AHG and sucrose, the non-growth rate was lower (0.040 $h^{-1}$) than that (0.061 $h^{-1}$) under the condition of 40 g/L of xylitol and sucrose (see FIGS. 6a and 6d). In addition, under the condition of 1.3 g/L of AHG and fructose, the non-growth rate was much lower (0.052 $h^{-1}$) than that (0.085 $h^{-1}$) under the condition of 40 g/L of xylitol and fructose (see FIGS. 6b and 6e). Similarly, under the condition of 2.5 g/L of AHG and maltose, the non-growth rate was much lower (0.031 $h^{-1}$) than that (0.045 $h^{-1}$) under the condition of 40 g/L of xylitol and maltose (see FIGS. 6c and 6f).

Under the conditions of xylitol and sucrose, the cell growth of *S. mutans* was decreased as the concentration of xylitol was increased (see FIG. 6d). However, xylitol did not completely inhibit the cell growth of *S. mutans* even at the maximum concentration, i.e., 40 g/L used in the present experiment (see FIG. 6d). In contrast, the cell growth of *S. mutans* was completely inhibited at a much lower concentration, i.e., 5 g/L, of AHG under the sucrose condition (see FIG. 6a).

From the above results, it can be seen that AHG inhibits not only glucose metabolism, but also the metabolism of other fermentable sugars, i.e., sucrose, fructose, and maltose. Unusually, among the four fermentable sugars, the inhibitory effect of AHG was the most significant in the fructose condition. This seems to be due to a greater structural similarity between AHG and fructose compared to other sugars, i.e., a ketose with a furanose ring.

The present invention can be used as medicines, foods, oral hygienic agents, and the like in fields for preventing, alleviating, or treating oral diseases.

What is claimed is:

1. A method for treating an oral disease comprising: administering a pharmaceutically effective amount of 3,6-anhydro-L-galactose to a subject in need thereof.

2. The method of claim 1, wherein the oral disease is any one selected from dental caries, gingivitis, periodontitis, oral mucous ulcers, halitosis, and xerostomia.

3. The method of claim 1, wherein 3,6-anhydro-L-galactose prevents or treats an oral disease by inhibiting the growth of one or more oral microorganisms selected from the group consisting of *Streptococcus mutans, Streptococcus oralis, Streptococcus sanguinis, Fusobacterium nulcleatum, Porphyromonas gingivalis, Actinomyces viscosus, Actinobacillus actinomycetemcomitans*, and *Candida albicans*, and acid production.

4. The method of claim 3, wherein the oral microorganisms use one or more carbon sources selected from the group consisting of glucose, sucrose, fructose, and maltose.

* * * * *